United States Patent
Wang et al.

(10) Patent No.: US 10,131,654 B2
(45) Date of Patent: Nov. 20, 2018

(54) PYRAZOLE COMPOUNDS AND METHODS OF USE THEREOF

(71) Applicant: TRANSLATIONAL DRUG DEVELOPMENT, LLC, Scottsdale, AZ (US)

(72) Inventors: Tong Wang, Scottsdale, AZ (US); Stephen Gately, Scottsdale, AZ (US)

(73) Assignee: Translational Drug Development, LLC, Scottsdale, AZ (US)

( * ) Notice: Subject to any disclaimer, the term of this patent is extended or adjusted under 35 U.S.C. 154(b) by 198 days.

(21) Appl. No.: 14/772,616

(22) PCT Filed: Mar. 7, 2014

(86) PCT No.: PCT/US2014/021880
§ 371 (c)(1),
(2) Date: Sep. 3, 2015

(87) PCT Pub. No.: WO2014/138616
PCT Pub. Date: Sep. 12, 2014

(65) Prior Publication Data
US 2016/0009702 A1    Jan. 14, 2016

Related U.S. Application Data

(60) Provisional application No. 61/775,014, filed on Mar. 8, 2013.

(51) Int. Cl.
| | |
|---|---|
| *C07D 417/10* | (2006.01) |
| *C07D 401/10* | (2006.01) |
| *C07D 405/14* | (2006.01) |
| *C07D 231/12* | (2006.01) |
| *C07D 403/10* | (2006.01) |

(52) U.S. Cl.
CPC ......... *C07D 417/10* (2013.01); *C07D 231/12* (2013.01); *C07D 401/10* (2013.01); *C07D 403/10* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 5,521,207 A | 5/1996 | Graneto | |
| 6,156,781 A | 12/2000 | Talley et al. | |
| 2004/0192930 A1* | 9/2004 | Talley | C07D 231/12 548/375.1 |
| 2006/0105961 A1 | 5/2006 | Masferrer | |

FOREIGN PATENT DOCUMENTS

WO    WO 1995/015316 A1 *    6/1995

OTHER PUBLICATIONS

Greenwald, RB. et al. Drug Delivery Systems: Water Soluble Taxol 2'-Poly(ethylene glycol) Ester Prodrugs—Design and in Vivo Effectiveness. J. Med. Chem. 1996, vol. 39, p. 425.*
Testa, B. et al. Lessons Learned from Marketed and Investigational Prodrugs. J. Med. Chem. 2004, vol. 47(10), p. 2393.*
Penning, TD. et al. Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celeoxib). J. Med. Chem. 1997, vol. 40, p. 1351.*
Poppe, L. et al. Stereochemistry and Stereoselective Synthesis. Wiley. 2016, p. 25.*
Taïri-Kellou, S. et al., Internet Electronic Journal of Molecular Design 2008, vol. 7, pp. 161-185.*
International Search Report issued in Application No. PCT/US2014/021880 dated Sep. 18, 2014.
International Preliminary Report on Patentability issued in Application No. PCT/US2014/021880 dated Sep. 8, 2015.
Organ et al. "Combining the use of solid-supported transition metal catalysis with microwave irradiation in solution—phase parallel library synthesis," Molecular Diversity 7(2-4): 211-227, 2003.

* cited by examiner

*Primary Examiner* — Heidi Reese
(74) *Attorney, Agent, or Firm* — Rodney J. Fuller; Booth Udall Fuller, PLC

(57) ABSTRACT

The present invention comprises compounds of Formula I and their use in the inhibition of cell proliferation in therapeutic treatments. Pharmaceutical compositions comprising at least one compound of Formula I and at least one pharmaceutical excipient are disclosed, as well as methods of using compounds of Formula I and pharmaceutical compositions thereof for treatment of hyper-proliferative diseases and other disorders.

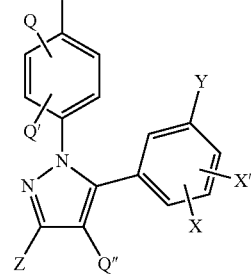

Formula I

18 Claims, No Drawings

PYRAZOLE COMPOUNDS AND METHODS OF USE THEREOF

CROSS-REFERENCE TO RELATED APPLICATIONS

This application claims priority to U.S. Provisional Patent Application Ser. No. 61/775,014, filed Mar. 8, 2013, which is incorporated herein it its entirety.

FIELD OF THE INVENTION

The present invention generally discloses new pyrazole compounds and more specifically discloses new pyrazole compounds useful for the treatment of cancer.

BACKGROUND OF THE INVENTION

Cancer is a group of diseases characterized by uncontrolled growth and spread of abnormal cells. If the spread is not controlled, it can result in death. Cancer is the second leading cause of death in the United States after heart disease. The American Cancer Society estimated that in 2012 there were 1.3 million new cases of cancer and 555,000 cancer-related deaths. Overall mortality rates have declined by 1% per year during the 1990s. There are currently over 9 million living Americans who have been diagnosed with cancer; and the NIH estimates the direct medical costs of cancer as $60 billion per year.

Typical treatment modalities useful in the treatment of cancer include chemotherapy, radiotherapy and surgery (see, for example, Stockdale, 1998, "Principles of Cancer Subject Management", in Scientific American: Medicine, vol. 3, Rubenstein and Federman, eds., Chapter 12, Section IV). All of these approaches pose significant drawbacks for the subject. Surgery, for example, can be contraindicated due to the health of the subject or can be unacceptable to the subject. Additionally, surgery may not successfully remove all neoplastic tissue. Chemotherapy involves the administration of cytotoxic chemical agents which are associated with a broad spectrum of undesirable side effects, including alopecia, nausea and vomiting, hematoxicity, neurotoxicity, nephrotoxicity, cardiotoxicity and hepatotoxicity. In addition, cancer cells commonly develop resistance to most anticancer agents, thus rendering chemotherapy ineffective over time.

There is a significant need in the art for novel compounds, compositions, and methods that are useful for treating cancer or neoplastic disease with increased selectivity and decreased toxicity.

SUMMARY OF THE INVENTION

The present invention generally comprises novel heterocyclic compounds based on a 1,5-diphenylpyrazole framework, pharmaceutical compositions comprising at least one of these compounds, and methods for treating cancer, or other proliferative disease, comprising administering at least one 1,5-diphenylpyrazole compound, or a pharmaceutical composition thereof, to a subject in need thereof.

DETAILED DESCRIPTION OF THE INVENTION

The present invention comprises compounds having Formula (I):

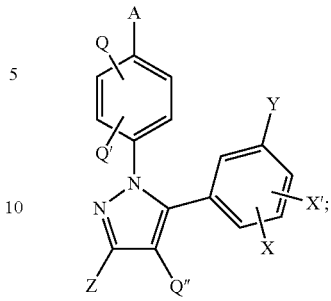

Formula I all salts, prodrugs, tautomers, and isomers thereof, wherein:
A is independently selected from $-SO_2NR^1R^2$ or $-C(O)NHOH$;
X and X' are independently selected from hydrogen, deuterium, halo, $C_1$-$C_6$ alkyl, $C_3$-$C_7$ cycloalkyl, aryl, heterocyclyl, $-OR^3$, $-CN$, $-C(O)OR^3$, $-OC(O)R^3$, $-NR^3R^4$, $-NHC(O)R^3$, $-NHSO_2R^3$, $-C(O)NHR^3$, $-SR^3$, $-SO_2R^3$ or $-SO_2NR^3R^4$; or X and X', taken together with the aryl C atoms to which they are attached, form a carbocyclic or heterocyclic ring;
Y is independently selected from halo, $C_1$-$C_6$ alkyl, $C_3$-$C_7$ cycloalkyl, aryl or heterocyclyl;
Z is independently selected from $C_1$-$C_6$ alkyl, $C_3$-$C_7$ cycloalkyl, $-C(O)OR^3$ or $-C(O)NR^3R^4$;
Q and Q' are independently selected from hydrogen, deuterium, halo, $C_1$-$C_6$ alkyl, $C_3$-$C_7$ cycloalkyl, $-OR^3$, $-CN$, $-C(O)OR^3$, $-OC(O)R^3$, $-NR^3R^4$, $-NHC(O)R^3$, $-NHSO_2R^3$, $-C(O)NHR^3$, $-SR^3$, $-SO_2R^3$ or $-SO_2NR^3R^4$;
Q" is independently selected from hydrogen, deuterium, halo, $C_1$-$C_6$ alkyl, $C_3$-$C_7$ cycloalkyl, $-OR^3$, $-CN$, $-C(O)OR^3$, $-OC(O)R^3$, $-NR^3R^4$, $-NHC(O)R^3$, $-NHSO_2R^3$, $-C(O)NHR^3$, $-SR^3$, $-SO_2R^3$ or $-SO_2NR^3R^4$;
$R^1$ and $R^2$ are independently selected from hydrogen, deuterium, $C_1$-$C_6$ alkyl, $C_3$-$C_7$ cycloalkyl, $-C(O)(C_1$-$C_6$ alkyl) or $-C(O)(C_3$-$C_7$ cycloalkyl); or $R^1$ and $R^2$, taken together with the N atom to which they are attached, form a heterocyclic ring; and
$R^3$ and $R^4$ are independently selected from hydrogen, deuterium, $C_1$-$C_6$ alkyl or $C_3$-$C_7$ cycloalkyl; or $R^3$ and $R^4$, taken together with the N atom to which they are attached, form a heterocyclic ring.

In various embodiments, the present invention comprises compounds of Formula I wherein Z is $-CF_3$.

In various embodiments, the present invention comprises compounds of Formula I wherein A is independently selected from $-SO_2NH_2$, $-SO_2NHC(O)CH_3$ or $-C(O)NHOH$.

In various embodiments, the present invention comprises compounds of Formula I wherein Z is independently selected from $-CH_3$, -cyclopropyl, $-CHF_2$, $-CH_2F$, $-CH_2CH_3$, -isopropyl, $-CO_2CH_3$ or $-C(O)NH_2$.

In various embodiments, the present invention comprises compounds of Formula I wherein Y is independently selected from -isopropyl, -cyclopropyl, $-F$, $-Cl$, $-Br$, $-CH_3$, 4-pyridinyl, 3-pyridinyl, 2-pyridinyl, 4-pyrazolyl, or 3-pyrazolyl.

In various embodiments, the present invention comprises compounds of Formula I wherein at least one of X or X' is $-CH_3$, $-CH_2CH_3$, $-CF_3$, $-F$, $-Cl$, $-Br$, -isopropyl, -cyclopropyl, $-OCH_3$, $-CH_2N(CH_3)_2$, $-N(CH_3)_2$, —NHSO$_2$CH$_3$, —NHC(O)CH$_3$, —C(O)NH$_2$, 4-pyridinyl, 3-pyridinyl, 2-pyridinyl, 4-pyrazolyl or 3-pyrazolyl.

In various embodiments, the present invention comprises compounds of Formula II:

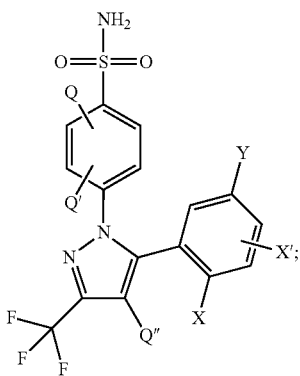

Formula II all salts, prodrugs, tautomers, and isomers thereof, wherein:
X is independently selected from hydrogen, deuterium, halo, C$_1$-C$_6$ alkyl, C$_3$-C$_7$ cycloalkyl, aryl, heterocyclyl, —OR$^3$, —CN, —C(O)OR$^3$, —OC(O)R$^3$, —NR$^3$R$^4$, —NHC(O)R$^3$, —NHSO$_2$R$^3$, —C(O)NHR$^3$, —SR$^3$, —SO$_2$R$^3$ or —SO$_2$NR$^3$R$^4$;
X' is independently selected from hydrogen, deuterium, halo, C$_1$-C$_6$ alkyl, C$_3$-C$_7$ cycloalkyl, —OR$^3$, —CN, —C(O)OR$^3$, —OC(O)R$^3$, —NR$^3$R$^4$, —NHC(O)R$^3$, —NHSO$_2$R$^3$, —C(O)NHR$^3$, —SR$^3$, —SO$_2$R$^3$ or —SO$_2$NR$^3$R$^4$; or X and X', taken together with the aryl C atoms to which they are attached, form a carbocyclic or heterocyclic ring;
Y is independently selected from halo, C$_1$-C$_6$ alkyl, C$_3$-C$_7$ cycloalkyl, aryl and heterocyclyl;
Q and Q' are independently selected from hydrogen, deuterium, halo, C$_1$-C$_6$ alkyl, C$_3$-C$_7$ cycloalkyl, —OR$^3$, —CN, —C(O)OR$^3$, —OC(O)R$^3$, —NR$^3$R$^4$, —NHC(O)R$^3$, —NHSO$_2$R$^3$, —C(O)NHR$^3$, —SR$^3$, —SO$_2$R$^3$ or —SO$_2$NR$^3$R$^4$;
Q" is independently selected from hydrogen, deuterium, halo, C$_1$-C$_6$ alkyl, C$_3$-C$_7$ cycloalkyl, —OR$^3$, —CN, —C(O)OR$^3$, —OC(O)R$^3$, —NR$^3$R$^4$, —NHC(O)R$^3$, —NHSO$_2$R$^3$, —C(O)NHR$^3$, —SR$^3$, —SO$_2$R$^3$, or —SO$_2$NR$^3$R$^4$; and
R$^3$ and R$^4$ are independently selected from hydrogen, deuterium, C$_1$-C$_6$ alkyl or C$_3$-C$_7$ cycloalkyl; or R$^3$ and R$^4$, taken together with the N atom to which they are attached, form a heterocyclic ring.

Definitions

As used herein, "halo" includes any halogen substituent. Examples include, but are not limited to, F, Cl, Br, or I.

As used herein, "alkyl" includes any straight or branched, saturated or unsaturated hydrocarbon radical, any of which can comprise "optional substitution." Examples of alkyl groups include, but are not limited to, methyl, ethyl, propyl, isopropyl, butyl, sec-butyl, tert-butyl, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, propynyl, 1- or 2-pentynyl groups, 1- or 2-butynyl groups, or 1-, 2- or 3-hexynyl groups, and the like. Optional substitution on the alkyl groups herein can include any applicable chemical moiety. Examples of optional substitution include, but are not limited to, the following substituents: halo, —O—(C$_1$-C$_6$ alkyl), —OH, —CN, —C(O)OR', —OC(O)R', —NHR', —N(R')$_2$, —NHC(O)R', —S(O)R' or —C(O)NHR' groups. The groups denoted R' above include an —H or any unsubstituted —C$_1$-C$_6$ alkyl, examples of which are listed above.

As used herein, "cycloalkyl" includes any 3-, 4-, 5-, 6-, or 7-membered non-aromatic carbocyclic ring, any of which can comprise "optional substitution." Examples of cycloalkyl groups include, but are not limited to, cyclopropyl, cyclobutyl, cyclopentyl, cyclopentadienyl, cyclohexyl, cyclohexenyl, cycloheptyl, cycloheptanyl, 1,3-cyclohexadienyl, 1,4-cyclohexadienyl, 1,3-cycloheptadienyl, and 1,3,5-cycloheptatrienyl groups, and the like. Examples of optional substitution for a cycloalkyl group herein include, but are not limited to, the following substituents: halo, C$_1$-C$_6$ alkyl, —OR', —CN, —C(O)OR', —OC(O)R', —NHR', —N(R')$_2$, —NHC(O)R' or —C(O)NHR' groups. The groups denoted R' above include an —H or any unsubstituted C$_1$-C$_6$ alkyl, examples of which are listed above.

As used herein, "aryl" includes any phenyl or naphthyl group, any of which can comprise "optional substitution." Examples of optional substitution for any aryl group herein include, but are not limited to, halo, C$_1$-C$_6$ alkyl, —OR', —CN, —C(O)OR', —OC(O)R', —NHR', —N(R')$_2$, —NHC(O)R' or —C(O)NHR' groups. The groups denoted R' above include an —H or any unsubstituted C$_1$-C$_6$ alkyl, examples of which are listed above.

As used herein, a "heterocycle" or "heterocyclic ring" can be any optionally substituted saturated, unsaturated or aromatic cyclic moiety wherein said cyclic moiety is interrupted by at least one heteroatom selected from oxygen (O), sulfur (S) or nitrogen (N). As used herein, "heterocyclyl" refers to a heterocyclic radical as a substituent group, being attached to another atom from any C or heteroatom present on the heterocyclic ring. For example, "pyridinyl" includes 2-pyridinyl, 3-pyridinyl and 4-pyridinyl substituent groups. Heterocycles may be monocyclic or polycyclic. Exemplary optional substitution on any heterocyclic group within the scope of the present invention include halogen (e.g. Br, Cl, I or F), cyano, nitro, oxo, amino, C$_{1-4}$ alkyl (e.g., CH$_3$, C$_2$H$_5$, isopropyl) C$_{1-4}$ alkoxy (e.g., OCH$_3$, OC$_2$H$_5$), halogenated C$_{1-4}$ alkyl (e.g., CF$_3$, CHF$_2$), halogenated C$_{1-4}$ alkoxy (e.g., OCF$_3$, OC$_2$F$_5$), C(O)OH, C(O)O—C$_{1-4}$ alkyl, C(O)—C$_{1-4}$ alkyl, C$_{1-4}$ alkyl —S— (e.g., CH$_3$S, C$_2$H$_5$S), halogenated C$_{1-4}$ alkyl —S— (e.g., CF$_3$S, C$_2$F$_5$S), benzyloxy, and pyrazolyl.

Examples of heterocycles include but are not limited to: azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl. Further examples of heterocyclic systems may be found in Katritzky, Handbook of Heterocyclic Chemistry.

The invention further comprises any physiochemical or stereochemical form that the compounds disclosed herein may assume. Such forms include, for example, (a) Isomers, Prodrugs, and Active Metabolites (b) Tautomers, Stereoisomers, Regioisomers, and Solvated Forms (c) Prodrugs and Metabolites (d) Pharmaceutically acceptable salts and (e) Polymorphic forms. Amorphous forms lack a distinguishable crystal lattice and therefore lack an orderly arrangement of structural units. Many pharmaceutical compounds have amorphous forms, crystalline forms, or mixtures thereof. Methods of generating such chemical forms are known to one skilled in the art, in addition to the crystallographic methods to determine extent and type of crystallinity.

In some aspects of the invention, the compound is in the form of a pharmaceutically acceptable salt. Pharmaceutically acceptable salts include any salt derived from an organic or inorganic acid. Examples of such salts include but are not limited to the following: salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl)benzoic acid, 1-hydroxy-2-naphthoic acid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulfuric acid, mucic acid, 2-naphthalenesulphonic acid, pamoic acid, pantothenic acid, phosphanilic acid ((4-aminophenyl)phosphonic acid), picric acid, salicylic acid, stearic acid, succinic acid, tannic acid, tartaric acid, terephthalic acid, p-toluenesulphonic acid, 10-undecenoic acid, or any other such acid now known or yet to be disclosed. It will be appreciated that such salts, provided that they are pharmaceutically acceptable, may be used in therapy. Such salts can be prepared by reaction of the base compound with a suitable acid in a manner known by those skilled in the art.

The phrase, "pharmaceutically acceptable", as used herein, means that the indicated material does not have properties that would cause a reasonably prudent medical practitioner to avoid administration of the material to a patient, taking into consideration the disease or conditions to be treated and the respective route of administration. The phrase, for example, denotes any salt, ester, or salt of such ester, of such compound, or any other adduct or derivative which, upon administration to a patient, is capable of providing (directly or indirectly) a compound as otherwise described herein, or a metabolite or residue (MW>300) thereof. Pharmaceutically acceptable derivatives thus include, among others, pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention.

Also provided in the present invention is a pharmaceutical composition comprising at least one compound in accordance with the invention, or an isomer, tautomer, prodrug, salt, hydrate or other solvate thereof, and at least one pharmaceutically acceptable excipient or additive. Such compositions can comprise a particular physical form useful for administration to a subject in need of treatment. Pharmaceutical compositions herein optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

The present invention includes all pharmaceutically acceptable isotopically-labeled compounds of Formula I and Formula II wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of Formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula I and Formula II can generally be prepared by conventional techniques known to those skilled in the art or by processes analogous to those described in the accompanying Examples and Preparations using an appropriate isotopically-labeled reagent in place of the non-labeled reagent previously employed.

Methods for the preparation of pharmaceutical compositions in accordance with the present invention comprise formulating one or more of the present compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In various embodiments, pharmaceutical compositions comprising at least one compound of the present invention can take the form of a liquid, wherein the agents are present in solution, in suspension, or both. Typically when the composition is administered as a solution or suspension a first portion of the active compound may be present in solution, and a second portion of the agent present in particulate form, such as suspended in a liquid matrix. In some embodiments, a liquid composition includes a gel formulation. In other embodiments, the liquid composition is aqueous.

In various embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. In various embodiments, pharmaceutical compositions in accordance with the present invention can include a mucoadhesive polymer, such as for example carboxymethylcellulose (CMC), a carbomer (a thickening acrylic acid polymer, optionally cross-linked), poly(methylmethacrylate), polyacrylamide, polycarbophil, acrylic acid/butyl acrylate copolymer, other acrylate copolymers, sodium alginate and dextran.

In various embodiments, compounds of the present invention are formulated for oral administration by combining the active compound(s) with, e.g., pharmaceutically acceptable carriers or excipients. In various embodiments, the compounds of the present invention are formulated in oral dosage forms that include, for example, tablets, powders, pills, capsules, liquids, gels, syrups, elixirs, slurries, suspensions, and the like.

In various embodiments, pharmaceutical compositions for oral use are obtained by mixing one or more solid excipients with one or more of the compounds described herein, optionally grinding the resulting mixture, and processing the mixture of granules, after adding suitable auxiliaries, if desired, to obtain tablets. Suitable excipients include fillers such as sugars, (e.g. lactose, sucrose, mannitol, or sorbitol); cellulosic substances: (e.g., maize starch, wheat starch, rice starch, potato starch, gelatin, gum tragacanth, methylcellulose, microcrystalline cellulose, hydroxypropylmethylcellulose, sodium carboxymethylcellulose); or other materials such as, for example, polyvinylpyrrolidone ("povidone") or calcium phosphate. In specific embodiments, disintegrants can be added. Disintegrants include, for example, cross-linked croscarmellose sodium, polyvinylpyrrolidone, agar, alginic acid and sodium alginate.

In various embodiments, tablets can be provided with one or more suitable coatings. In specific embodiments, concentrated sugar solutions are used for coating the dosage form. Sugar solutions can optionally contain additional components, such as for example, gum arabic, talc, polyvinylpyrrolidone, carbopol polyacrylate gels, polyethylene glycol, titanium dioxide, lacquer solutions, organic solvents or solvent mixtures. Colorants can be added to the coatings for marketing or dose identification, or other purpose.

In various embodiments, therapeutically effective amounts of at least one of the compounds of the present invention are formulated into other oral dosage forms. Oral dosage forms include push-fit capsules made of gelatin, as well as soft sealed capsules made of gelatin and a plasticizer, such as glycerol or sorbitol. In various embodiments, push-fit capsules contain the active ingredients mixed with one or more fillers. Fillers include, for example, lactose, binders such as starches, and/or lubricants such as talc or magnesium stearate and, optionally, stabilizers. In various other embodiments, soft capsules can contain one or more active compounds dissolved or suspended in a suitable liquid. Suitable liquids include, for example, one or more fatty oils, glycerin, glycerides, liquid paraffin, or various polyethylene glycols.

In various embodiments, therapeutically effective amounts of at least one of the compounds of the present invention are formulated for buccal or sublingual administration. Formulations suitable for buccal or sublingual administration include, for example, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers.

In various embodiments, the pharmaceutical compositions of the present invention comprise forms suitable for parenteral injection as sterile suspensions, solutions or emulsions, in oily or aqueous vehicles. Parenteral injection formulations optionally contain excipients such as suspending, stabilizing and/or dispersing agents. In specific embodiments, pharmaceutical compositions for parenteral administration include aqueous solutions of the active compounds in water-soluble form. In additional embodiments, suspensions of the active compounds are prepared as oily injection suspensions. Suitable lipophilic solvents or vehicles for use in the pharmaceutical compositions described herein include, for example, fatty acid blends such as those found in natural oils such as peanut oil, fatty acid esters, mono-, di- and triglycerides, or liposomes. In various embodiments, aqueous injection suspensions contain substances which increase the viscosity of the suspension, such as sodium CMC, sorbitol or dextran. Optionally, the suspension can include suitable stabilizers or other agents that increase the solubility of the compounds to allow for highly concentrated solutions. Alternatively, the active ingredient can be in a powdered form for later mixing with a suitable vehicle by the practitioner.

In various embodiments, the compounds of the present invention can be administered topically. The compounds described herein can be formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In various embodiments, the compounds of the present invention can be formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on-demand delivery of pharmaceutical agents. In additional embodiments, transdermal delivery of any of the compounds of the present invention can be accomplished using iontophoretic patches and the like. In certain embodiments, transdermal patches provide controlled delivery of the compounds of the present invention. In specific embodiments, the rate of absorption is slowed by using rate-controlling membranes or by trapping the compound within a polymer matrix or gel. In alternative embodiments, absorption, or permeability, enhancers are used to increase absorption. Absorption enhancers or carriers include absorbable pharmaceutically acceptable solvents that assist passage through the skin. For example, in various embodiments, transdermal devices can comprise a bandage having a backing member, a reservoir containing the compound optionally with carriers, optionally a rate controlling barrier, and means to secure the device to the skin.

Transdermal dosage forms can incorporate conventional pharmaceutically acceptable excipients. In various embodiments, the transdermal compositions can include at least one compound of the present invention, along with a penetration enhancer and an aqueous adjuvant. In addition, transdermal formulations can include components such as gelling agents, creams and ointment bases, and the like. A number of these bases are commercially available. In various embodiments, the transdermal composition can further include a woven or non-woven backing material to enhance absorption and prevent the removal of the transdermal formulation from the skin. In other embodiments, the transdermal compositions maintain a saturated or supersaturated state to promote diffusion into the skin.

In various embodiments, the compounds of the present invention can be formulated for administration by inhalation. Inhalation administration can include an intranasal spray. Various forms suitable for administration by inhalation include aerosols, mists or powders. Pharmaceutical compositions comprising compounds of the present invention can be conveniently delivered in the form of an aerosol spray presentation from pressurized packaging or a nebulizer, e.g. with the use of a propellant (e.g., dichlorodifluoromethane, trichlorofluoromethane, dichlorotetrafluoroethane, carbon dioxide, or the like). In various embodiments, the dosage unit of a pressurized aerosol is determined by selection of a valve that can meter the dose. In certain embodiments, capsules and cartridges of the composition can be provided for use within a pressurized delivery system. In various embodiments, the compounds of the present invention can be formulated into liquid compositions sprayable from non-aerosol packaging.

In various embodiments, the compounds of the present invention can be formulated into rectal compositions such as enemas, rectal gels, rectal foams, rectal aerosols, suppositories, jelly suppositories, or retention enemas, which contain suppository bases such as cocoa butter or other glycerides, in addition to synthetic polymers such as polyvinylpyrrolidone, PEG, and the like. Suppository forms can include a low-melting wax such as, but not limited to, a mixture of fatty acid glycerides.

Another aspect of the present invention comprises methods for treating hyper-proliferative diseases such as cancer, amongst other disorders, in a subject in need thereof, which comprises administering to the subject a treatment effective amount of at least one compound of the present invention, or a pharmaceutical composition thereof. The compounds described herein are useful in treating cancer and other disorders, alone or in combination with one or more additional compounds having anti-cancer properties.

Compounds of the present invention, and pharmaceutical compositions thereof, can be administered to a subject with a hyper-proliferative disease to inhibit the growth, development and/or metastasis of cancers, including solid tumors (e.g., breast, colon, pancreatic, CNS and head and neck cancers, among others) and various forms of leukemia, including leukemias and other cancers which can be resistant to other treatments, and generally for the treatment and prophylaxis of diseases or undesirable conditions.

The cancer treatment method of this invention involves administering, (as a single therapy or in combination with one or more other therapeutic agents and/or one or more agents for ameliorating side effects of therapy), a therapeutically effective amount of a compound of the present invention, such as in a pharmaceutical composition having any of the physical forms described above, to a human or animal in need of treatment in order to inhibit, slow or reverse the growth, development or spread of cancer, including solid tumors or other forms of cancer such as a leukemia, in the recipient. Such administration constitutes a method for the treatment or prophylaxis of diseases by one of the disclosed compounds, a pharmaceutically acceptable derivative thereof, or a pharmaceutical composition thereof "Administration" of a compound of this invention encompasses the delivery to a recipient of a compound of the sort described herein, or a prodrug or other pharmaceutically acceptable derivative thereof, using any suitable formulation or route of administration, as discussed herein. Typically the compound is administered one or more times per month, often one or more times per week, e.g. daily, every other day, 5 days/week, etc. Compounds of the present invention, and pharmaceutical compositions thereof, can be administered by oral, transdermal and intravenous routes, amongst others.

Organic Synthetic Techniques

Various synthetic approaches may be used to produce the compounds described herein, including, for example, those approaches depicted schematically below. The practitioner will appreciate that protecting groups may be used in these approaches. "Protecting groups" are moieties that are used to temporarily block chemical reaction at a potentially reactive site (e.g., an amine, hydroxy, thiol, aldehyde, etc.) so that a reaction can be carried out selectively at another site in a multifunctional compound. In various embodiments, a protecting group reacts selectively in good yield to give a protected substrate that is suitable for the planned reactions. The protecting group can then be selectively removable in good yield by readily available reagents that do not unduly attack the other functional groups present. The protecting group preferably forms a readily separable derivative (more preferably without the generation of new chiral centers). Also, the protecting group preferably has a minimum of additional functionality to avoid the complication of further sites of reaction. A wide variety of protecting groups and strategies, reagents and conditions for deploying and removing them are known in the art. See, e.g., "Protective Groups in Organic Synthesis" Third Ed. Greene, T. W. and Wuts, P. G., Eds., John Wiley & Sons, New York: 1999. For additional background information on protecting group methodologies (materials, methods and strategies for protection and removal) and other synthetic chemistry transformations useful in producing the compounds described herein, see in R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), incorporated herein by reference.

A wide array of organic synthetic techniques exists in the art to facilitate the synthesis of the compounds of the present invention. The practitioner has a well-established literature of relevant chemical transformations, recovery and purification technologies to draw upon, in combination with the information contained in the examples which follow, for guidance on synthetic strategies, protecting groups, and other materials and methods useful for the synthesis, recovery and characterization of the compounds of this invention. Many of these organic synthetic methods are described in detail in standard reference sources utilized by those skilled in the art. One example of such a reference is March, 1994, Advanced Organic Chemistry; Reactions, Mechanisms and Structure, N.Y., McGraw Hill.

Also, one may choose reagents enriched for a desired isotope, e.g. deuterium in place of hydrogen, to create compounds of this invention containing such isotope(s). Compounds containing deuterium in place of hydrogen in one or more locations, or containing various isotopes of C, N, P and O, are encompassed by this invention and may be used, for instance, for studying metabolism and/or tissue distribution of the compounds or to alter the rate or path of metabolism or other aspects of biological functioning.

The pyrazole compounds of the present invention can be synthesized using the methods described below, together with synthetic methods known in the art of synthetic organic chemistry, or by a variation thereon as appreciated by those skilled in the art. Preferred methods include, but are not limited to those described below. The reactions are performed in a solvent system appropriate to the reagents and materials employed and suitable for the transformation being effected. It will be understood by those skilled in the art of organic synthesis that the functionality present on the molecule should be consistent with the transformations proposed. This will sometimes require some judgment in modifying the order of the synthetic steps or the selection of a particular process scheme over another in order to obtain a desired compound of the invention.

In various embodiments, compounds of the present invention may be prepared as outlined in Scheme 1 below, supplemented and/or modified with any necessary methods known to those skilled in the art:

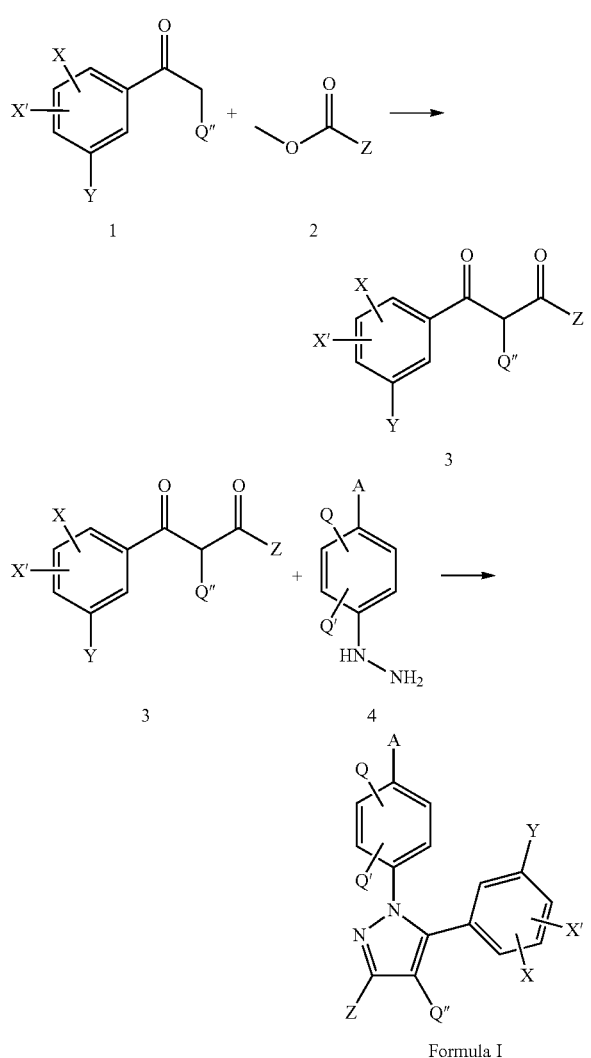

In accordance with general Scheme 1, various substituted phenyl ketones having structure 1 are reacted with an alkyl ester 2 in the presence of a base such as sodium methoxide, and in a solvent such as dimethyl sulfoxide, to produce compounds having formula 3. Coupling of compounds 3 with various phenyl hydrazines having structure 4, in ethanol, affords compounds of Formula I.

When the Y group in Formula I is halo (such as —Br in structure 5), further chemical transformations can be used to reach other compounds of the present invention, as shown in Scheme 2 below:

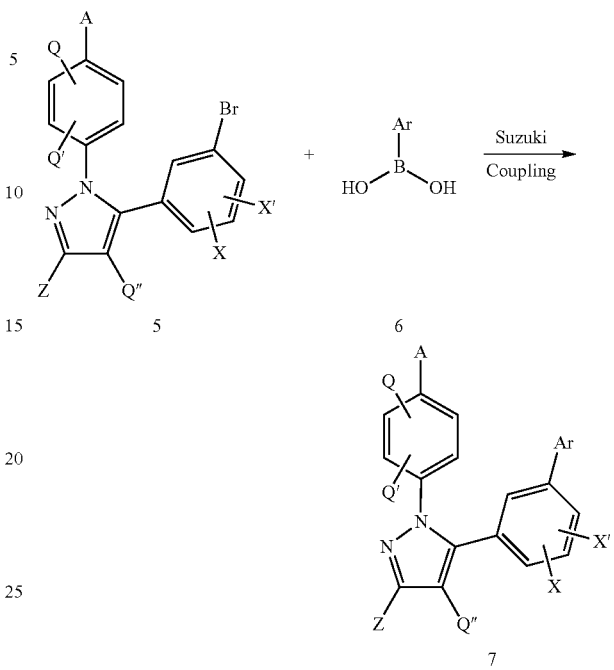

Suzuki Coupling of a compound of structure 5 and a boronic acid 6 provides compounds 7. The "Ar" of the boronic acid 6 should not be construed as limiting. The boronic acid 6 can comprise, for example, any substituted or unsubstituted aryl boronic acid or heterocyclic boronic acid. Heterocyclic boronic acids 6 can include, for example, substituted or unsubstituted 2-, 3-, or 4-pyridineboronic acid or a substituted or unsubstituted 3- or 4-pyrazoleboronic acid.

Regarding the synthetic examples described herein, solvents used in the particular reactions include polar and non-polar solvents known to those of skill in the art, including polar aprotic and polar protic solvents. Polar solvents include, without limitation, protic solvents such as methanol, ethanol, isopropyl alcohol, t-butanol, n-butanol, acetic acid, formic acid or water, or aprotic solvents such as tetrahydrofuran (THF), acetonitrile, dioxane, methylene chloride, dimethylsulfoxide (DMSO), acetone, N,N-dimethylformamide (DMF), N,N-dimethylacetamide (DMA), ethyl acetate, 1,2-dimethoxyethane (DME), 1,2-dichloroethane, chloroform, 1,2-dichloroethane, or pyridine. Polar solvents include a mixture of water with any of the above, or a mixture of any two or more of the above. Apolar solvents include, without limitation, toluene, benzene, chlorobenzene, xylenes and hexanes.

Regarding the synthetic examples described herein, reductive transformations can include, without limitation, a reducing agent such as catalytic reducing agents comprising hydrogen and transition metal catalysts such as palladium, platinum, rhodium, etc. (e.g. Pt/Acetic acid/$H_2$); a mixture of trifluoroacetic acid and triethylsilane, borane tetrahydrofuran complex, diborane, borane dimethylsulfide complex, and a combination of sodium borohydride and boron trifluoride; metals such as reduced iron, zinc powder, magnesium etc.; metal hydrogen complex compounds such as alkali metal borohydrides (for example, potassium borohydride, sodium borohydride, lithium borohydride, zinc borohydride, sodium triacetoxyborohydride, etc.), lithium aluminum hydride, etc.; metal hydrides such as sodium hydride, etc.; organo tin compounds (triphenyltin hydride, etc.); and metal salts such as nickel compounds, zinc compounds, tin compounds (for example tin(II) chloride), and samarium iodide/pivalic acid/hexamethylphosphoric triamide.

Regarding the synthetic examples described herein, oxidative transformations can include, without limitation, an oxidizing agent such as Dess-Martin reagent, TEMPO (2,2, 6,6-tetramethylpiperidine-N-oxide), DDQ (2,3-dichloro-5, 6-dicyano-1,4-benzoquinone), PDC (pyridinium dichromate), PCC (pyridinium chlorochromate), pyridine-$SO_3$, chromium trioxide, p-nitroperbenzoic acid, magnesium monoperoxyphthalate, sodium periodate, potassium periodate, hydrogen peroxide, urea peroxide, alkali metal bromates, cumene hydroperoxide, tert-butyl peroxide, peracids such as performic acid, peracetic acid, pertrifluoroacetic acid, perbenzoic acid, m-chloroperbenzoic acid, o-carboxyperbenzoic acid and the like; sodium metaperiodate, bichromic acid; bichromates such as sodium bichromate, potassium bichromate; permanganic acid; permanganates such as potassium permanganate, sodium permanganate; and lead salts such as lead tetraacetate.

EXAMPLES

Examples related to the present invention are described below. The examples are intended to be illustrative, and are not limiting or restrictive to the scope of the invention. In some examples, the mass spectrometry result indicated for a compound may have more than one value due to the isotope distribution of an atom in the molecule, such as a compound having a bromo or chloro substituent.

Example 1

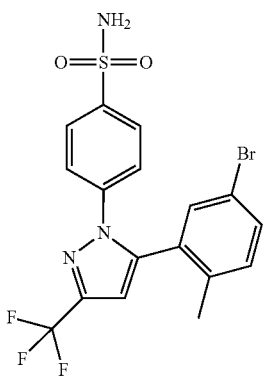 [SMILES: Cc1ccc(Br)cc1-c1cc(C(F)(F)F)nn1-c1ccc(S(N)(=O)=O)cc1]

Step 1

To a solution of 5-bromo-2-methylbenzaldehyde (300 mg, 1.51 mmol) in THF at 0° C. was added methylmagnesium chloride solution (3 M, 0.65 mL, 1.91 mmol) dropwise. The reaction was stirred at 0° C. for 3 hrs, quenched with ammonium chloride solution and extracted with ethyl acetate. The organic layer was dried, concentrated and purified by Biotage column chromatography to give 1-(5-bromo-2-methylphenyl)ethanol (270 mg, 83%);

Step 2

To a solution of 1-(2-bromo-5-methylphenyl)ethanol (270 mg, 1.26 mmol) in dichloromethane was added $MnO_2$ (1.10 g, 12.6 mmol). The mixture was stirred at room temperature for 20 hrs and filtered. The filtrate was concentrated and purified by Biotage column chromatography to give 5'-bromo-2'-methylacetophenone (171 mg, 64%);

Step 3

To a solution of 5'-bromo-2'-methylacetophenone (100 mg, 0.47 mmol) and ethyl trifluoroacetate (133 mg, 0.94 mmol) in DMSO was added sodium methoxide (76 mg, 1.41 mmol). The reaction was heated to 50° C., stirred for 5 hr and quenched with ammonium acetate solution. The mixture was extracted with ethyl acetate. The organic layer was dried and concentrated to give crude 1-(5-bromo-2-methylphenyl)-4,4,4-trifluorobutane-1,3-dione (110 mg);

Step 4

A solution of 1-(5-bromo-2-dimethylaminophenyl)-4,4,4-trifluorobutane-1,3-dione (110 mg, 0.35 mmol) and 4-hydrazinylbenzenesulfonamide HCl salt (87 mg, 0.39 mmol) in ethanol was heated to reflux overnight and concentrated. The residue was purified by Biotage column chromatography to give Example 1 (130 mg, 81%). MS (ESI Found M+1: 461); $^1$H NMR (CDCl$_3$, 300 Hz): δ 8.05-8.02 (d, 2H J=6.3 Hz), 7.67-7.65 (dd, 1H, $J_1$=1.5 Hz, $J_2$=6.3 Hz), 7.60-7.57 (m, 3H), 7.27-7.25 (d, 1H, J=6.3 Hz), 6.86 (s, 1H), 4.97 (s, 2H), 2.04 (s, 3H).

Example 2

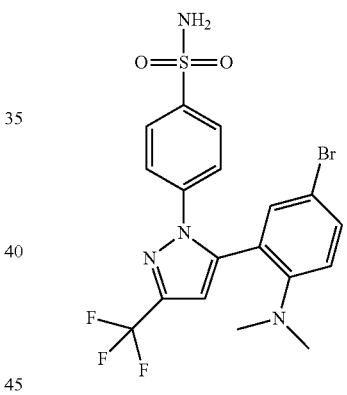

Step 1

To a solution of 1-(5-bromo-2-fluorophenyl)ethanone (217 mg, 1.0 mmol) and dimethylamine HCl salt (121 mg, 1.5 mmol) in acetonitrile was added potassium carbonate (276 mg, 2.0 mmol). The reaction was heated to 60° C., stirred for 5 hr and cooled to room temperature. The reaction mixture was partitioned between ethyl acetate and water. The organic layer was dried, concentrated and give crude 1-(5-bromo-2-dimethylaminophenyl)ethanone;

Step 2

To a solution of 1-(5-bromo-2-dimethylaminophenyl)ethanone (111 mg, 0.46 mmol) and ethyl trifluoroacetate (130 mg, 0.92 mmol) in DMSO was added sodium methoxide (75 mg, 1.38 mmol). The reaction was heated to 50° C., stirred for 5 hrs and quenched with ammonium acetate solution. The mixture was extracted with ethyl acetate. The organic layer was dried and concentrated. The residue was purified by Biotage column chromatography to give 1-(5-bromo-2-dimethylaminophenyl)-4,4,4-trifluorobutane-1,3-dione (77 mg, 50%);

Step 3

A solution of 1-(5-bromo-2-dimethylaminophenyl)-4,4,4-trifluorobutane-1,3-dione (60 mg, 0.18 mmol) and 4-hydrazinylbenzenesulfonamide HCl salt (45 mg, 0.20 mmol) in ethanol was heated to reflux overnight and concentrated. The residue was purified by Biotage column chromatography to give Example 2 (68 mg, 78%). MS (ESI Found M+1=490); $^1$H NMR (CDCl$_3$, 300 Hz): 7.83-7.81 (d, 2H J=5.4 Hz), 7.52-7.51 (s, 1H), 7.44-7.42 (dd, 1H J1=1.5 Hz, J2=6.6 Hz), 7.36-7.33 (d, 2H, J=5.4 Hz), 6.77 (s, 1H), 6.70-6.68 (d, 1H J=6.6 Hz), 5.13 (b, 2H), 2.54-2.51 (b, 4H), 2.10 (s, 6H).

Example 3

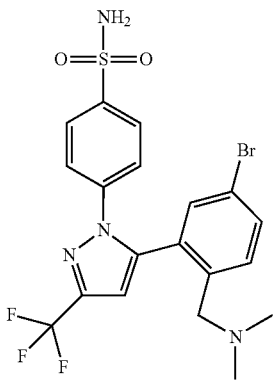 [SMILES: CN(C)Cc1ccc(Br)cc1-c1cc(C(F)(F)F)nn1-c1ccc(S(N)(=O)=O)cc1]

Step 1

To a mixture of Example 2 (20 mg, 0.043 mmol) and N-bromosuccimide (8.5 mg, 0.048 mmol) in carbon tetrachloride was added catalytic amount of azobisisobutyronitrile (AIBN).

The reaction was heated to 55° C., stirred for 24 hrs and cooled room temperature. The mixture was diluted with dichloromethane and washed with sodium bicarbonate solution. The organic layer was dried, concentrated and the residue purified by Biotage column chromatography to give 4-{5-[5-bromo-2-(bromomethyl)phenyl]-3-(trifluoromethyl)-1H-pyrazol-1-yl}benzenesulfonamide (9.6 mg, 41%);

Step 2

To a solution of 4-{5-[5-bromo-2-(bromomethyl)phenyl]-3-(trifluoromethyl)-1H-pyrazol-1-yl}benzenesulfonamide (5.0 mg, 0.0093 mmol) and dimethylamine HCl salt (1.1 mg, 0.015 mmol) in acetonitrile was added cesium carbonate (4.6 mg, 0.015 mmol). The reaction was heated to 50° C. and stirred for 3 hrs. The mixture was partitioned between ethyl acetate and water. The organic layer was dried, concentrated and the residue purified by Biotage column chromatography to give Example 3 (3.3 mg, 71%). MS (ESI Found M+1: 504).

Table 1 lists compounds prepared using the reaction schemes as described in Example 1, 2 and 3:

TABLE 1

Compounds 4-10

| ID | Structure | MS (M + 1) |
|---|---|---|
| 4 | 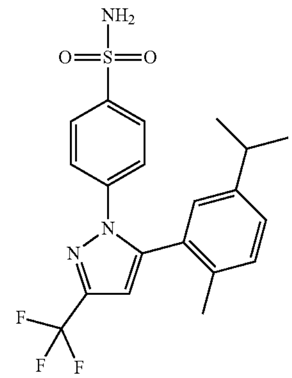 [SMILES: Cc1ccc(C(C)C)cc1-c1cc(C(F)(F)F)nn1-c1ccc(S(N)(=O)=O)cc1] | 424 |
| 5 | 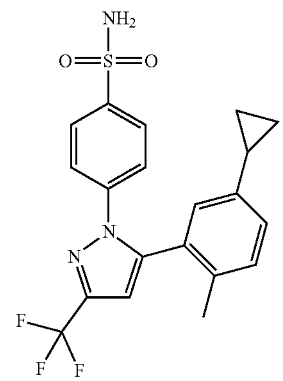 [SMILES: Cc1ccc(C2CC2)cc1-c1cc(C(F)(F)F)nn1-c1ccc(S(N)(=O)=O)cc1] | 422 |
| 6 | 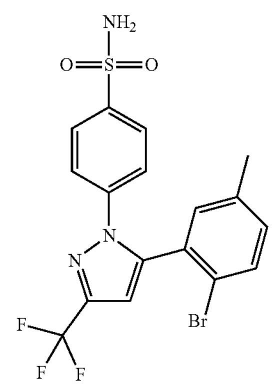 [SMILES: Cc1ccc(Br)c(-c2cc(C(F)(F)F)nn2-c2ccc(S(N)(=O)=O)cc2)c1] | 461 |
| 7 | 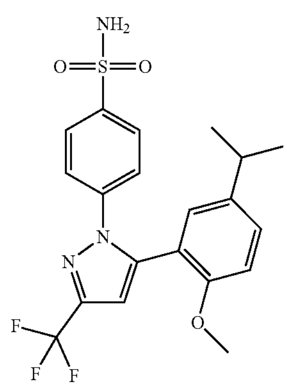 [SMILES: COc1ccc(C(C)C)cc1-c1cc(C(F)(F)F)nn1-c1ccc(S(N)(=O)=O)cc1] | 440 |

TABLE 1-continued

Compounds 4-10

| ID | Structure | MS (M + 1) |
|---|---|---|
| 8 | 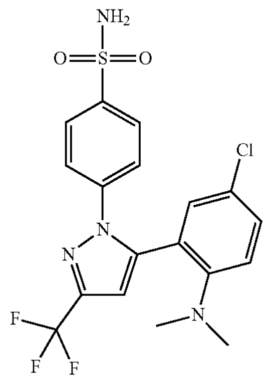 [SMILES: CN(C)c1ccc(Cl)cc1-c1cc(C(F)(F)F)nn1-c1ccc(S(N)(=O)=O)cc1] | 445 |
| 9 | 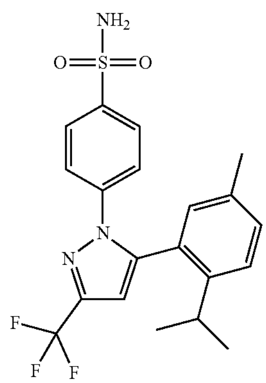 [SMILES: Cc1ccc(C(C)C)c(-c2cc(C(F)(F)F)nn2-c2ccc(S(N)(=O)=O)cc2)c1] | 424 |
| 10 | 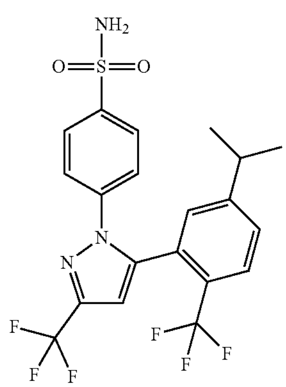 [SMILES: CC(C)c1ccc(C(F)(F)F)c(-c2cc(C(F)(F)F)nn2-c2ccc(S(N)(=O)=O)cc2)c1] | 478 |

Example 11

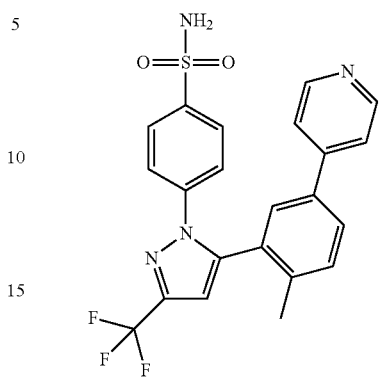

Step 1

A mixture of Example 1 (25 mg, 0.054 mmol), 4-pyridineboronic acid (32 mg, 0.19 mmol), [1,1'-bis(diphenylphosphino)ferrocene]dichloropalladium(II) (Pd(dppf)Cl$_2$) (2.0 mg, 0.003 mmol) and potassium phosphate (63 mg, 0.3 mmol) in dioxane was heated to reflux under nitrogen atmosphere and stirred for 16 hrs. The reaction was cooled to room temperature, diluted with ethyl acetate and washed with brine. The organic layer was dried, concentrated and the residue purified by Biotage column chromatography to give Example 11 (19 mg, 77%). MS (ESI Found M+1: 459); $^1$H NMR (CD$_3$OD, 300 Hz): δ 8.54-8.53 (d, 2H J=4.5 Hz), 7.88-7.86 (d, 2H, J=6.3 Hz), 7.78-7.76 (d, 1H, J=6.3 Hz), 7.70 (s, 1H), 7.62-7.61 (d, 2H, J=4.5 Hz), 7.50-7.48 (d, 2H, J=6.3 Hz), 7.42-7.40 (d, 1H, J=6.3 Hz), 6.97 (s, 1H), 2.06 (s, 3H).

Example 12

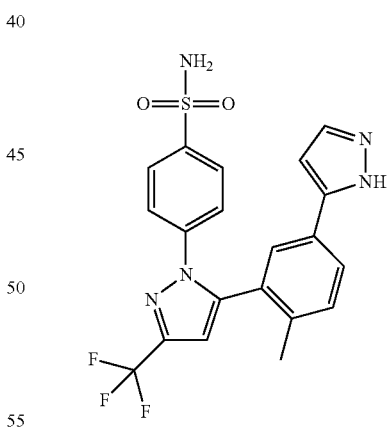

Step 1

A mixture of Example 1 (20 mg, 0.044 mmol), 1H-pyrazole-3-boronic acid (30 mg, 0.26 mmol), Pd(dppf)Cl$_2$ (2 mg, 0.003 mmol) and potassium phosphate (126 mg, 0.53 mmol) in dioxane was heated to reflux under nitrogen atmosphere and stirred for 16 hrs. The reaction was cooled to room temperature, diluted with ethyl acetate and washed with brine. The organic layer was dried, concentrated and the residue purified by Biotage column chromatography to give Example 12 (7.3 mg, 37%). MS (ESI Found M+1: 448); $^1$H NMR (CD$_3$OD, 300 Hz): δ 7.89-7.86 (m, 2H), 7.79-7.77 (d, 1H, J=6.0 Hz), 7.75 (s, 1H), 7.65 (s, 1H), 7.52-7.49 (m, 2H), 7.32-7.30 (d, 1H, J=6.0 Hz), 6.92 (s, 1H), 6.64-6.63 (d, 1H, J=1.8 Hz), 1.99 (s, 3H).

Table 2 lists compounds prepared using the reaction schemes as described in Examples 11 and 12:

TABLE 2

| Compounds 13-64 | | |
|---|---|---|
| ID | Structure | MS (M + 1) |
| 13 | | 445 |
| 14 | | 473 |
| 15 | | 487 |
| 16 | | 485 |
| 17 | | 488 |
| 18 | | 502 |
| 19 | | 475 |

TABLE 2-continued

Compounds 13-64

| ID | Structure | MS (M + 1) |
|----|-----------|------------|
| 20 | 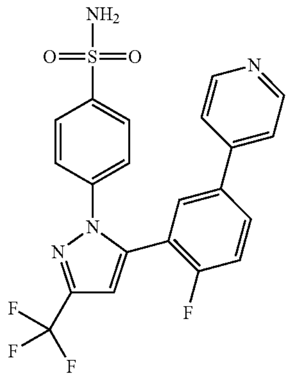 [SMILES: NS(=O)(=O)c1ccc(-n2nc(C(F)(F)F)cc2-c2cc(-c3ccncc3)ccc2F)cc1] | 463 |
| 21 | 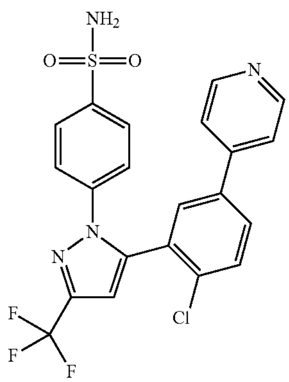 [SMILES: NS(=O)(=O)c1ccc(-n2nc(C(F)(F)F)cc2-c2cc(-c3ccncc3)ccc2Cl)cc1] | 479 |
| 22 | 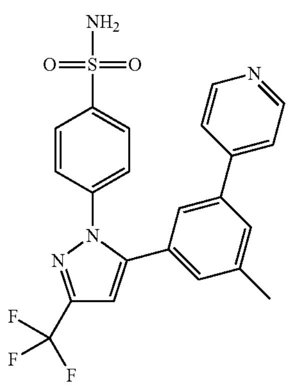 [SMILES: Cc1cc(-c2ccncc2)cc(-c2cc(C(F)(F)F)nn2-c2ccc(S(N)(=O)=O)cc2)c1] | 459 |
| 23 | 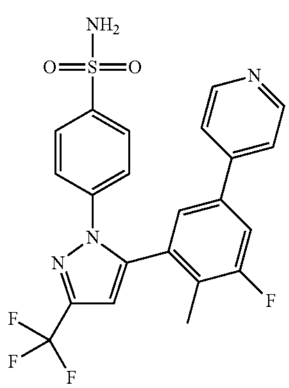 [SMILES: Cc1c(F)cc(-c2ccncc2)cc1-c1cc(C(F)(F)F)nn1-c1ccc(S(N)(=O)=O)cc1] | 477 |
| 24 | | 506 |
| 25 | | 502 |
| 26 | | 538 |
| 27 | | 488 |

TABLE 2-continued

Compounds 13-64

| ID | Structure | MS (M + 1) |
|----|-----------|------------|
| 28 | 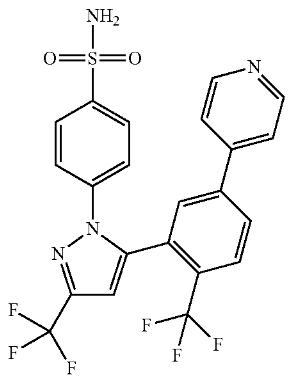 [SMILES: NS(=O)(=O)c1ccc(-n2nc(C(F)(F)F)cc2-c2cc(-c3ccncc3)ccc2C(F)(F)F)cc1] | 513 |
| 29 | 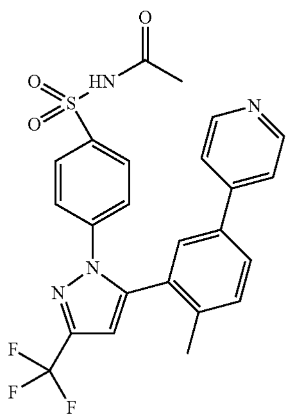 [SMILES: CC(=O)NS(=O)(=O)c1ccc(-n2nc(C(F)(F)F)cc2-c2cc(-c3ccncc3)ccc2C)cc1] | 501 |
| 30 | 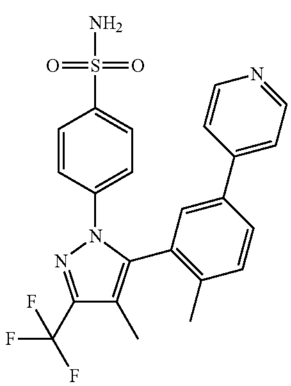 | 473 |
| 31 | 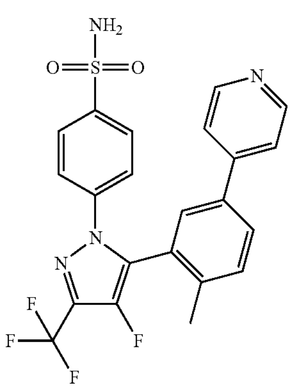 [SMILES: Cc1ccc(-c2ccncc2)cc1-c1c(F)c(C(F)(F)F)nn1-c1ccc(S(N)(=O)=O)cc1] | 477 |
| 32 | | 477 |
| 33 | | 477 |
| 34 | | 434 |
| 35 | | 452 |

TABLE 2-continued

Compounds 13-64

| ID | Structure | MS (M + 1) |
|----|-----------|------------|
| 36 | 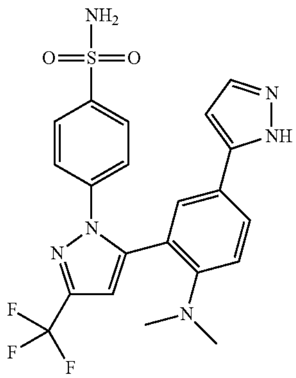 [SMILES: CN(C)c1ccc(-c2ccn[nH]2)cc1-c1cc(C(F)(F)F)nn1-c1ccc(S(N)(=O)=O)cc1] | 477 |
| 37 | 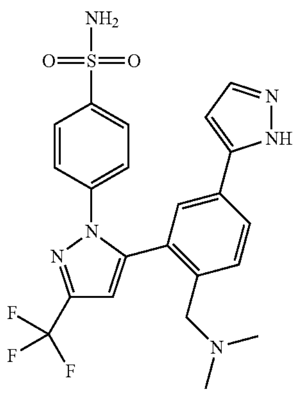 [SMILES: CN(C)Cc1ccc(-c2ccn[nH]2)cc1-c1cc(C(F)(F)F)nn1-c1ccc(S(N)(=O)=O)cc1] | 491 |
| 38 | 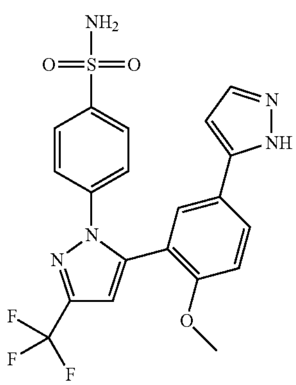 [SMILES: COc1ccc(-c2ccn[nH]2)cc1-c1cc(C(F)(F)F)nn1-c1ccc(S(N)(=O)=O)cc1] | 464 |
| 39 | 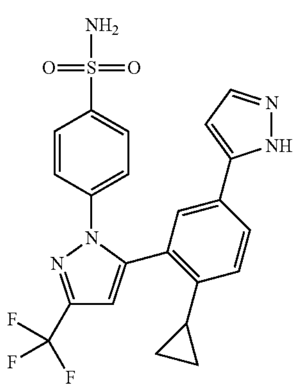 [SMILES: NS(=O)(=O)c1ccc(-n2nc(C(F)(F)F)cc2-c2cc(-c3ccn[nH]3)ccc2C2CC2)cc1] | 474 |
| 40 | | 476 |
| 41 | | 462 |
| 42 | | 466 |
| 43 | | 466 |

TABLE 2-continued
Compounds 13-64
| ID | Structure | MS (M + 1) |
|---|---|---|
| 44 | 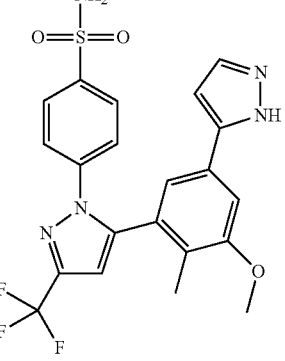 | 478 |
| 45 | 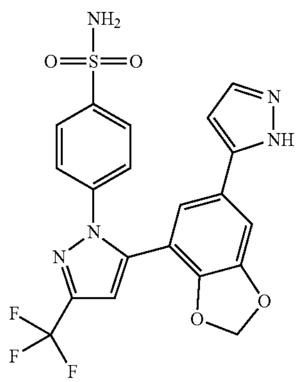 [SMILES: NS(=O)(=O)c1ccc(-n2nc(C(F)(F)F)cc2-c2cc(-c3ccn[nH]3)cc3c2OCO3)cc1] | 478 |
| 46 | 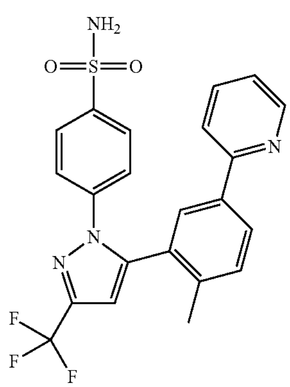 [SMILES: Cc1ccc(-c2ccccn2)cc1-c1cc(C(F)(F)F)nn1-c1ccc(S(N)(=O)=O)cc1] | 459 |
| 47 | 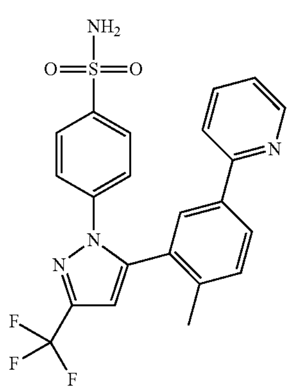 [SMILES: Cc1ccc(-c2ccccn2)cc1-c1cc(C(F)(F)F)nn1-c1ccc(S(N)(=O)=O)cc1] | 459 |
| 48 | 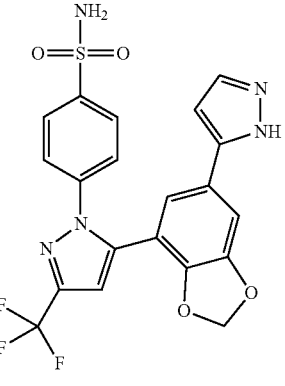 | 460 |
| 49 | | 460 |
| 50 | | 448 |
| 51 | | 462 |

TABLE 2-continued

Compounds 13-64

| ID | Structure | MS (M + 1) |
|---|---|---|
| 52 | 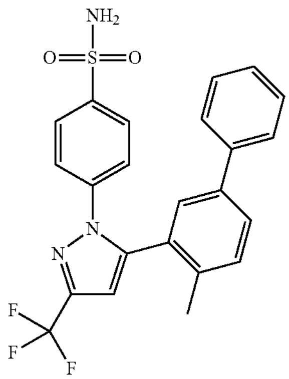 [SMILES: Cc1ccc(-c2ccccc2)cc1-c1cc(C(F)(F)F)nn1-c1ccc(S(N)(=O)=O)cc1] | 458 |
| 53 | 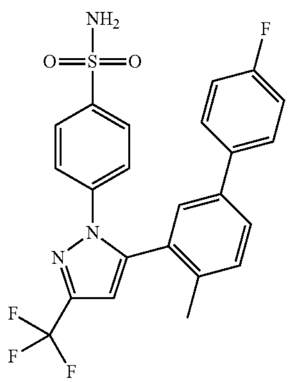 [SMILES: Cc1ccc(-c2ccc(F)cc2)cc1-c1cc(C(F)(F)F)nn1-c1ccc(S(N)(=O)=O)cc1] | 476 |
| 54 | 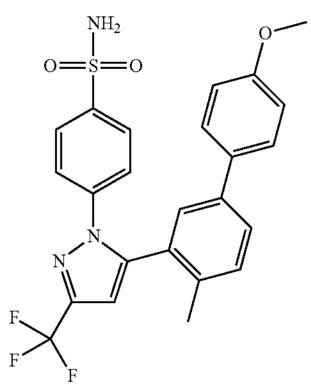 [SMILES: COc1ccc(-c2ccc(C)c(-c3cc(C(F)(F)F)nn3-c3ccc(S(N)(=O)=O)cc3)c2)cc1] | 488 |
| 55 | 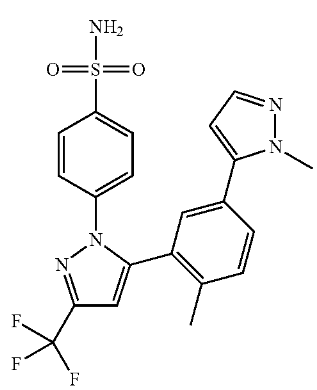 [SMILES: Cc1ccc(-c2ccnn2C)cc1-c1cc(C(F)(F)F)nn1-c1ccc(S(N)(=O)=O)cc1] | 462 |
| 56 | | 465 |
| 57 | | 465 |
| 58 | | 477 |
| 59 | | 479 |

TABLE 2-continued

Compounds 13-64

| ID | Structure | MS (M + 1) |
|---|---|---|
| 60 | 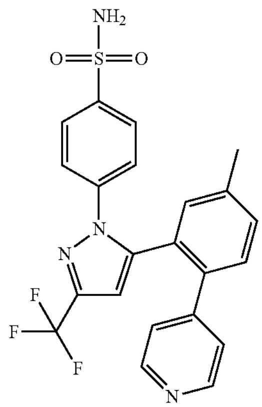 [SMILES: Cc1ccc(-c2ccncc2)c(-c2cc(C(F)(F)F)nn2-c2ccc(S(N)(=O)=O)cc2)c1] | 459 |
| 61 | 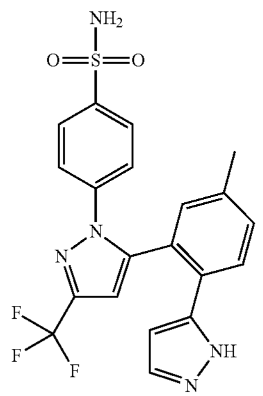 [SMILES: Cc1ccc(-c2ccn[nH]2)c(-c2cc(C(F)(F)F)nn2-c2ccc(S(N)(=O)=O)cc2)c1] | 448 |
| 62 | 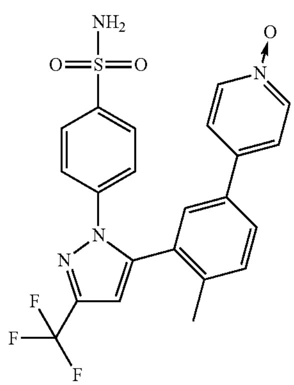 [SMILES: Cc1ccc(-c2cc[n+]([O-])cc2)cc1-c1cc(C(F)(F)F)nn1-c1ccc(S(N)(=O)=O)cc1] | 475 |
| 63 | 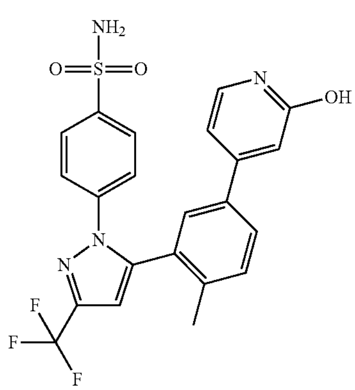 [SMILES: Cc1ccc(-c2ccnc(O)c2)cc1-c1cc(C(F)(F)F)nn1-c1ccc(S(N)(=O)=O)cc1] | 475 |
| 64 | | 477 |

Example 65

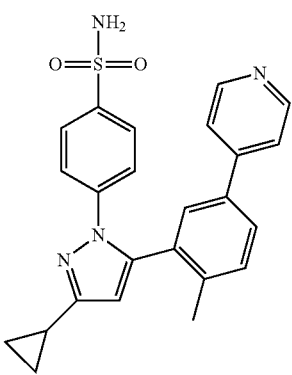 [SMILES: Cc1ccc(-c2ccncc2)cc1-c1cc(C2CC2)nn1-c1ccc(S(N)(=O)=O)cc1]

Step 1

To a solution of 1-(5-bromo-2-methylphenyl)ethanone (100 mg, 0.47 mmol) and methyl cyclopropylcarboxylate (187 mg, 1.88 mmol) in DMSO was added sodium methoxide (76 mg, 1.38 mmol). The reaction was heated to 50° C., stirred for 5 hrs and quenched with ammonium acetate solution. The mixture was extracted with ethyl acetate. The organic layer was dried and concentrated. The residue was purified by Biotage column chromatography to give 1-(5-bromo-2-methylphenyl)-3-cyclopropylpropane-1,3-dione (106 mg, 80%);

Step 2

A solution of 1-(5-bromo-2-methylphenyl)-3-cyclopropylpropane-1,3-dione (30 mg, 0.11 mmol) and 4-hydrazinylbenzenesulfonamide HCl salt (25 mg, 0.11 mmol) in ethanol was heated to reflux overnight and concentrated. The residue was purified by Biotage column chromatography to give 4-(5-(5-bromo-2-methylphenyl)-3-cyclopropyl-1H-pyrazol-1-yl)benzenesulfonamide (25 mg, 53%);

Step 3

A mixture of 4-(5-(5-bromo-2-methylphenyl)-3-cyclopropyl-1H-pyrazol-1-yl)benzenesulfonamide (25 mg, 0.058 mmol), 4-pyridineboronic acid (32 mg, 0.19 mmol), Pd(dppf)Cl$_2$ (2.0 mg, 0.003 mmol) and potassium phosphate (63 mg, 0.3 mmol) in dioxane was heated to reflux under nitrogen atmosphere and stirred for 16 hrs. The reaction was cooled to room temperature, diluted with ethyl acetate and washed with brine. The organic layer was dried, concentrated and the residue purified by Biotage column chromatography to give Example 65 (13 mg, 52%). MS (ESI Found M+1: 431).

Table 3 lists compounds prepared using the reaction schemes as described in Example 65:

TABLE 3

Compounds 66-73

| ID | Structure | MS (M + 1) |
| --- | --- | --- |
| 66 | | 405 |
| 67 | | 441 |
| 68 | | 423 |
| 69 | 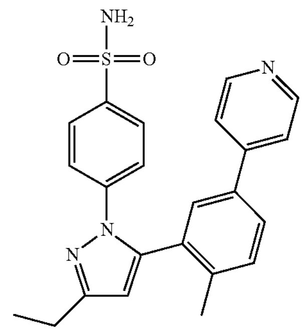 [SMILES: CCc1cc(-c2cc(-c3ccncc3)ccc2C)n(-c2ccc(S(N)(=O)=O)cc2)n1] | 419 |
| 70 | 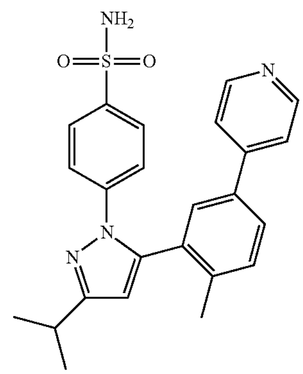 [SMILES: Cc1ccc(-c2ccncc2)cc1-c1cc(C(C)C)nn1-c1ccc(S(N)(=O)=O)cc1] | 433 |
| 71 | 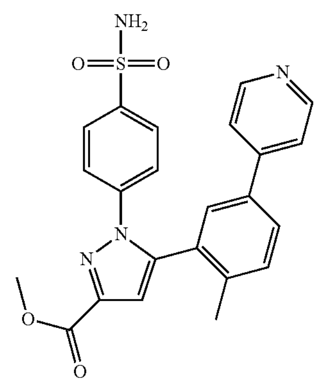 [SMILES: COC(=O)c1cc(-c2cc(-c3ccncc3)ccc2C)n(-c2ccc(S(N)(=O)=O)cc2)n1] | 449 |
| 72 | 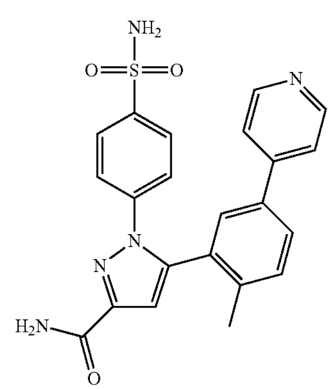 [SMILES: Cc1ccc(-c2ccncc2)cc1-c1cc(C(N)=O)nn1-c1ccc(S(N)(=O)=O)cc1] | 434 |

TABLE 3-continued

Compounds 66-73

| ID | Structure | MS (M + 1) |
|---|---|---|
| 73 | (sulfonamide phenyl-pyrazole-cyclopropyl-methylphenyl-pyrazole structure) | 420 |

Example 74

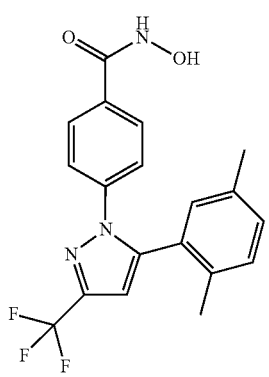 [SMILES: Cc1ccc(C)c(-c2cc(C(F)(F)F)nn2-c2ccc(C(=O)NO)cc2)c1]

Step 1

To a solution of 1-(2,5-dimethylphenyl)ethanone (200 mg, 1.35 mmol) and ethyl trifluoroacetate (383 mg, 2.70 mmol) in DMSO was added sodium methoxide (218 mg, 4.05 mmol). The reaction was heated to 50° C., stirred for 5 hrs and quenched with ammonium acetate solution. The mixture was extracted with ethyl acetate. The organic layer was dried and concentrated. The residue was purified by Biotage column chromatography to give 1-(2,5-dimethyl-phenyl)-4,4,4-trifluorobutane-1,3-dione (270 mg, 82%);

Step 2

A solution of 1-(5-bromo-2-dimethylaminophenyl)-4,4,4-trifluorobutane-1,3-dione (50 mg, 0.20 mmol) and ethyl 4-hydrazinylbenzoate (40 mg, 0.22 mmol) in ethanol was heated to reflux, stirred overnight and concentrated. The residue was purified by Biotage column chromatography to give ethyl 4-(5-(2,5-dimethylphenyl)-3-(trifluoromethyl)-1H-pyrazol-1-yl)benzoate (70 mg, 88%);

Step 3

To a solution of 4-(5-(2,5-dimethylphenyl)-3-(trifluoromethyl)-1H-pyrazol-1-yl)benzoate (70 mg, 0.18 mmol) and hydroxylamine (50% in water, 0.24 mL, 3.6 mmol) in THF/MeOH (5:1) was added sodium hydroxide solution (5 M, 0.1 mL, 0.5 mmol). The reaction was stirred for 12 hrs, neutralized with 1 M HCl and concentrated. The residue was partitioned between ethyl acetate and water. The organic layer was dried, concentrated and the residue purified by Biotage reverse phase C-18 column chromatography to give Example 74 (51 mg, 76%). MS (ESI Found M+1: 376); $^1$H NMR (DMSO-d6, 300 Hz): δ 9.09 (s, 1H), 7.74-7.72 (d, 2H J=6.6 Hz), 7.35-7.33 (d, 2H, J=6.6 Hz), 7.17-7.14 (m, 3H), 7.09 (s, 1H), 2.24 (s, 3H), 1.90 (s, 3H).

Table 4 lists compounds prepared using the reaction schemes as described in Example 74:

TABLE 4

Compounds 75-78

| ID | Structure | MS (M + 1) |
|---|---|---|
| 75 | (N-hydroxybenzamide-pyrazole-cyclopropyl-2,5-dimethylphenyl) | 348 |
| 76 | (N-hydroxybenzamide-pyrazole-cyclopropyl-3-methyl-4-chlorophenyl) | 368 |
| 77 | (N-hydroxybenzamide-pyrazole-CF3-methylphenyl-pyridinyl) | 439 |

TABLE 4-continued

Compounds 75-78

| ID | Structure | MS (M + 1) |
|---|---|---|
| 78 | 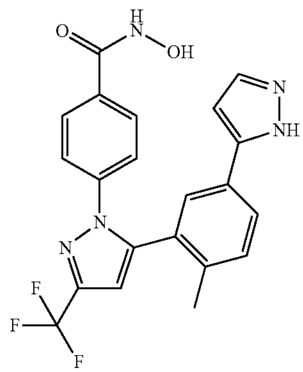 [SMILES: Cc1ccc(-c2ccn[nH]2)cc1-c1cc(C(F)(F)F)nn1-c1ccc(C(=O)NO)cc1] | 428 |

Efficacy Testing

Cell viability in the presence of varying concentrations of the above listed compounds at different time points was used to assess cytotoxicity and the effect of the compounds on cell proliferation. $IC_{50}$ (or percent activity) data for the compounds of the present invention in the AN3CA and/or A498 cell lines are summarized in Table 5 below.

Cell Viability Assay

Cell viability was measured by the CellTiter-Blue® cell viability assay Promega (Madison, Wis.). This procedure measures the conversion of the indicator dye (resazurin) to resorufin, an indicator of cell viability. Following treatment, growth media was removed and cells were incubated with 20 µl of CellTiter-Blue® Reagent and growth media for 1-4 hours at 37° C. Fluorescence values were measured at 535/590 nm using a Beckman-Coulter DTX-880 microplate reader.

Experimental Design

Single Agent Studies:

Cells were grown to 70% confluency, trypsinized, counted, and seeded in 96 well flat-bottom plates at a final concentration of $2.5 \times 10^3$-$5 \times 10^3$ cells/well (Day 0). Cells were allowed to incubate in growth media for 24 hours to allow for maximum adhesion. Treatment with the test agents or standard agents began on Day 1 and continued for 72 hours. At the 72 hour timepoint, treatment containing media was removed. Viable cell numbers were quantified by the CellTiter-Blue® cell viability assay as described above. Experiments were repeated at least twice with the same concentrations to determine growth inhibitory activity. Results from these studies were used to calculate an $IC_{50}$ value (concentration of drug that inhibits cell growth by 50 percent of control) for each compound.

Data Collection:

For single agent and combination studies, data from each experiment were collected and expressed as % Cell Growth using the following calculation:

$$\% \text{ Cell Growth} = (f_{test}/f_{vehicle}) \times 100$$

where $f_{test}$ is the fluorescence of the tested sample, and $f_{vehicle}$ is the fluorescence of the vehicle in which the drug is dissolved. Dose response graphs and $IC_{50}$ values were generated using Prism 4 software (GraphPad) using the following equation:

$$Y = (\text{Top} - \text{Bottom})/(1 + 10^{((\log IC50 - X) - \text{HillSlope})})$$

where X is the logarithm of concentration and Y is the response. Y starts at the Bottom and goes to Top with a sigmoid shape.

TABLE 5

| ID | $IC_{50}$ in A498 (µM) | $IC_{50}$ in AN3CA (µM) |
|---|---|---|
| 1 | 11 | 7.6 |
| 2 | 1.2 | 0.6 |
| 4 | 1.1 | 0.83 |
| 6 | 6.9 | 1.5 |
| 7 | 12 | 5.8 |
| 11 | 8.9 | 0.01 |
| 12 | 14 | 0.04 |
| 20 | | 3.0 |
| 22 | | 1.2 |
| 34 | 12 | 2.1 |
| 36 | | 9.1 |
| 46 | 10 | 9.1 |
| 73 | 7.9 | 3.3 |
| 76 | | 9.0 |

We claim:

1. A compound having the formula:

Formula I all salts, or tautomers thereof, wherein:

A is independently selected from —$SO_2NR^1R^2$ or —C(O)NHOH;

X is independently selected from halo, $C_1$-$C_6$ alkyl, $C_3$-$C_7$ cycloalkyl, aryl, heterocyclyl, —$OR^3$, —CN, —C(O)$OR^3$, —OC(O)$R^3$, —$NR^3R^4$, —NHC(O)$R^3$, —$NHSO_2R^3$, —C(O)$NHR^3$, —$SR^3$, —$SO_2R^3$ or —$SO_2NR^3R^4$;

X' is independently selected from hydrogen, deuterium, halo, $C_1$-$C_6$ alkyl, $C_3$-$C_7$ cycloalkyl, aryl, heterocyclyl, —$OR^3$, —CN, —C(O)$OR^3$, —OC(O)$R^3$, —$NR^3R^4$, —NHC(O)$R^3$, —$NHSO_2R^3$, —C(O)$NHR^3$, —$SR^3$, —$SO_2R^3$ or —$SO_2NR^3R^4$; or X and X', taken together with the aryl C atoms to which they are attached, form a carbocyclic or heterocyclic ring;

Y is independently selected from aryl or heterocyclyl;

Z is independently selected from $C_1$-$C_6$ alkyl, $C_3$-$C_7$ cycloalkyl, —C(O)$OR^3$ or —C(O)$NR^3R^4$;

Q and Q' are independently selected from hydrogen, deuterium, halo, $C_1$-$C_6$ alkyl, $C_3$-$C_7$ cycloalkyl, —$OR^3$, —CN, —C(O)$OR^3$, —OC(O)$R^3$, —$NR^3R^4$, —NHC(O)$R^3$, —$NHSO_2R^3$, —C(O)$NHR^3$, —$SR^3$, —$SO_2R^3$ or —$SO_2NR^3R^4$;

Q" is independently selected from hydrogen, deuterium, halo, $C_1$-$C_6$ alkyl, $C_3$-$C_7$ cycloalkyl, —$OR^3$, —CN, —C(O)$OR^3$, —OC(O)$R^3$, —$NR^3R^4$, —NHC(O)$R^3$, —$NHSO_2R^3$, —C(O)$NHR^3$, —$SR^3$, —$SO_2R^3$ or —$SO_2NR^3R^4$;

R[1] and R[2] are independently selected from hydrogen, deuterium, $C_1$-$C_6$ alkyl, $C_3$-$C_7$ cycloalkyl, —C(O)($C_1$-$C_6$ alkyl) or —C(O)($C_3$-$C_7$ cycloalkyl); or R[1] and R[2], taken together with the N atom to which they are attached, form a heterocyclic ring; and R[3] and R[4] are independently selected from hydrogen, deuterium, $C_1$-$C_6$ alkyl or $C_3$-$C_7$ cycloalkyl; or R[3] and R[4], taken together with the N atom to which they are attached, form a heterocyclic ring.

2. The compound of claim 1, wherein Z is $CF_3$.

3. The compound of claim 1, wherein A is —$SO_2NH_2$, —$SO_2NHC(O)CH_3$, or —C(O)NHOH.

4. The compound of claim 1, wherein Z is —$CH_3$, -cyclopropyl, —$CHF_2$, —$CH_2F$, —$CH_2CH_3$, -isopropyl, —$CO_2CH_3$, or —C(O)$NH_2$.

5. The compound of claim 1, wherein Y is 4-pyrazolyl or 3-pyrazolyl.

6. The compound of claim 1, wherein at least one of X or X' is —$CH_3$, —$CH_2CH_3$, —$CF_3$, —F, —Cl, —Br, -isopropyl, -cyclopropyl, —$OCH_3$, —$CH_2N(CH_3)_2$, —$N(CH_3)_2$, —$NHSO_2CH_3$, —NHC(O)$CH_3$, —C(O)$NH_2$, 4-pyridinyl-, 3-pyridinyl-, 2-pyridinyl-, 4-pyrazolyl-, or 3-pyrazolyl-.

7. A compound having the formula:

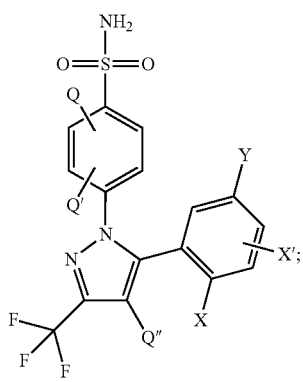

Formula II all salts, or tautomers thereof, wherein:
X is independently selected from hydrogen, deuterium, halo, $C_1$-$C_6$ alkyl, $C_3$-$C_7$ cycloalkyl, aryl, heterocyclyl, —OR[3], —CN, —C(O)OR[3], —OC(O)R[3], —NR[3]R[4], —NHC(O)R[3], —$NHSO_2$R[3], —C(O)NHR[3], —SR[3], —$SO_2$R[3], or —$SO_2$NR[3]R[4];
X' is independently selected from hydrogen, deuterium, halo, $C_1$-$C_6$ alkyl, $C_3$-$C_7$ cycloalkyl, —OR[3], —CN, —C(O)OR[3], —OC(O)R[3], —NR[3]R[4], —NHC(O)R[3], —$NHSO_2$R[3], —C(O)NHR[3], —SR[3], —$SO_2$R[3], or —$SO_2$NR[3]R[4]; or X and X', taken together with the aryl C atoms to which they are attached, form a carbocyclic or heterocyclic ring;
Y is independently selected from aryl or heterocyclyl;
Q and Q' are independently selected from hydrogen, deuterium, halo, $C_1$-$C_6$ alkyl, $C_3$-$C_7$ cycloalkyl, —OR[3], —CN, —C(O)OR[3], —OC(O)R[3], —NR[3]R[4], —NHC(O)R[3], $NHSO_2$R[3], —C(O)NHR[3], —SR[3], —$SO_2$R[3], or —$SO_2$NR[3]R[4];
Q" is independently selected from hydrogen, deuterium, halo, $C_1$-$C_6$ alkyl, $C_3$-$C_7$ cycloalkyl, —OR[3], —CN, —C(O)OR[3], —OC(O)R[3], —NR[3]R[4], —NHC(O)R[3], —$NHSO_2$R[3], —C(O)NHR[3], —SR[3], —$SO_2$R[3], or —$SO_2$NR[3]R[4]; and R[3] and R[4] are independently selected from hydrogen, deuterium, $C_1$-$C_6$ alkyl, or $C_3$-$C_7$ cycloalkyl; or R[3] and R[4], taken together with the N atom to which they are attached, form a heterocyclic ring.

8. The compound of claim 7, wherein Y is 4-pyridinyl-.

9. The compound of claim 7, wherein Y is 3-pyridinyl-.

10. The compound of claim 7, wherein Y is 2-pyridinyl-.

11. The compound of claim 7, wherein Y is 3-pyrazolyl-.

12. The compound of claim 7, wherein Y is 4-pyrazolyl-.

13. A compound selected from the group consisting of:

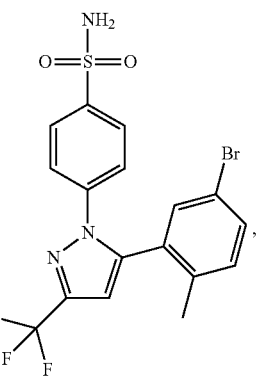

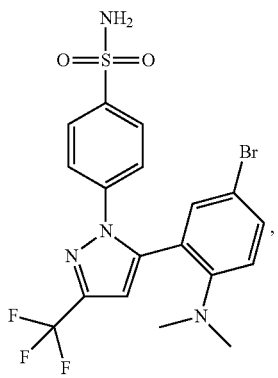

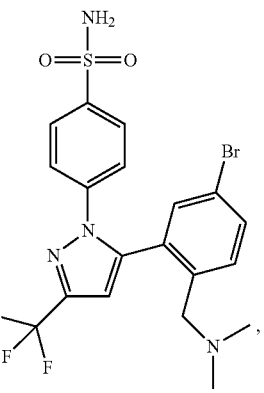

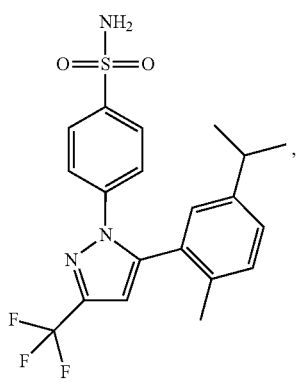
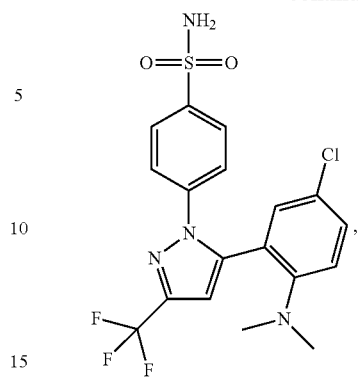
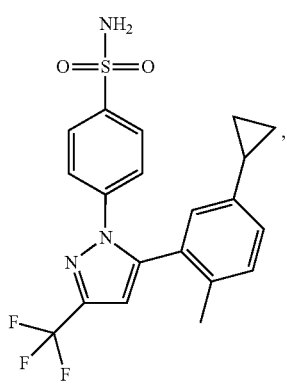
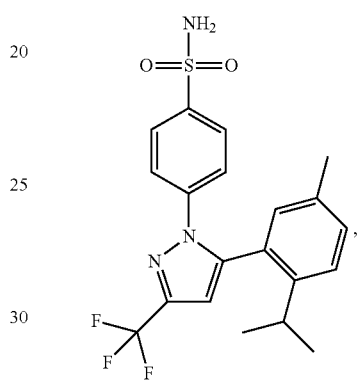
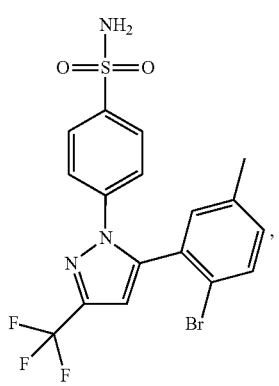
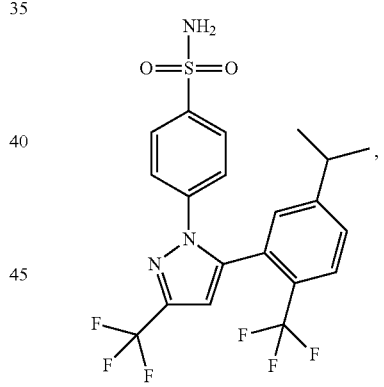
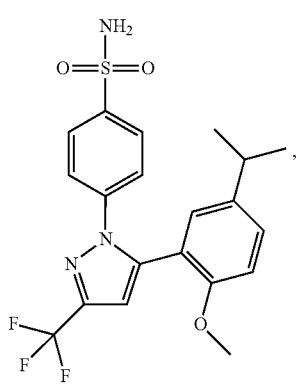
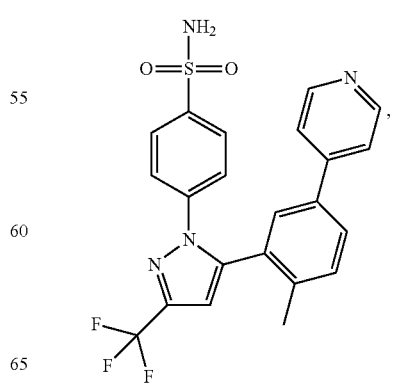

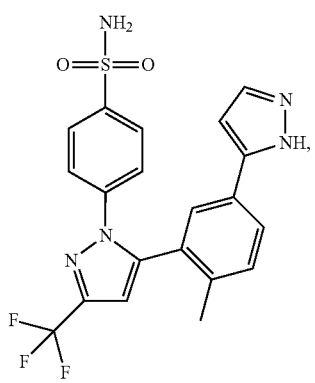
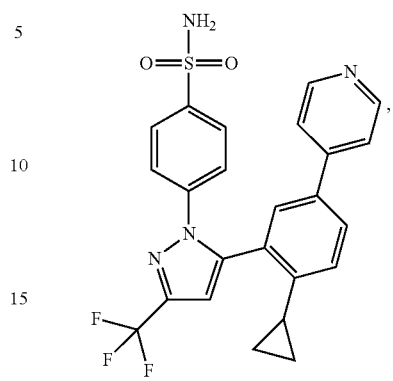
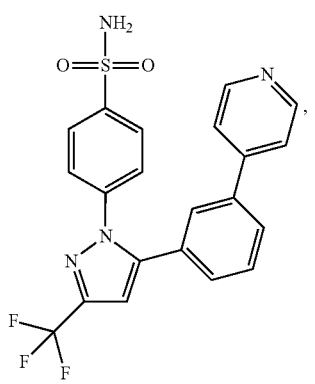
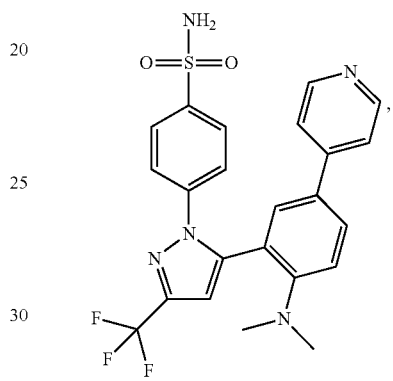
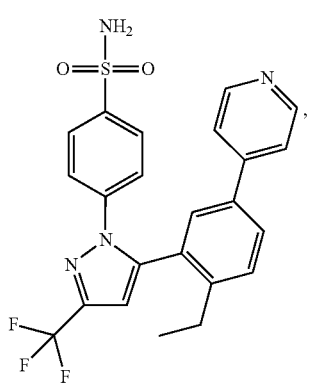
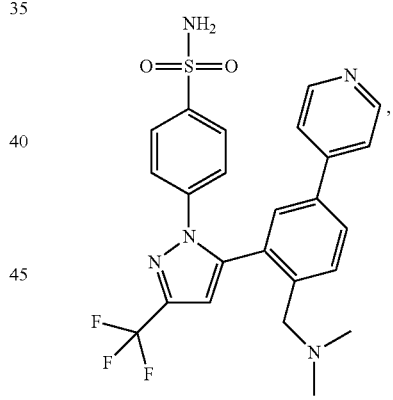
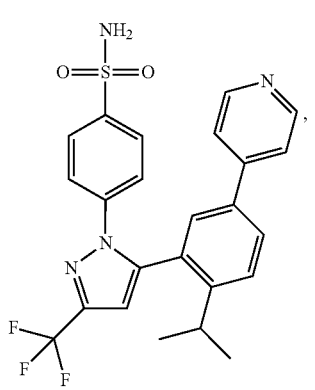
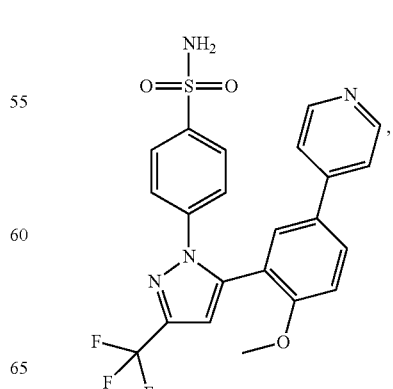

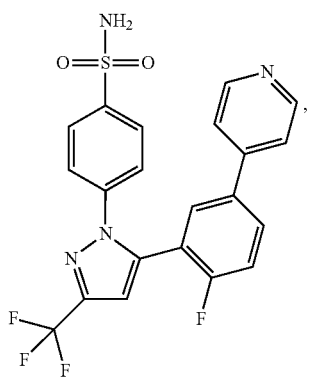
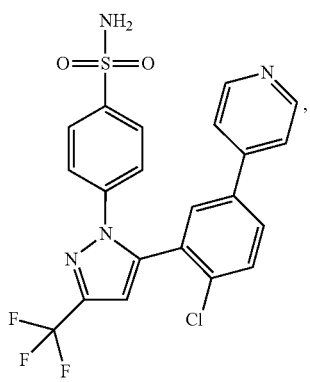
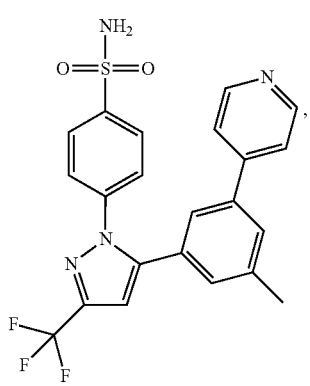
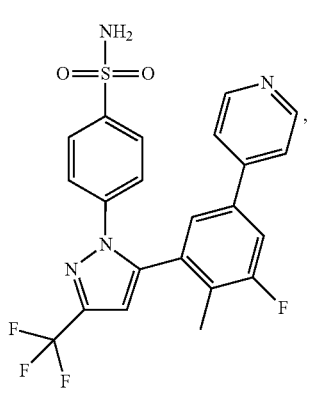
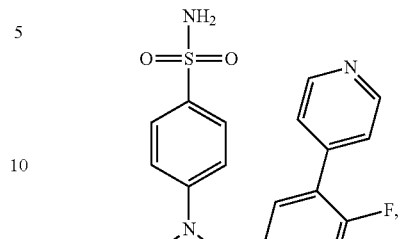
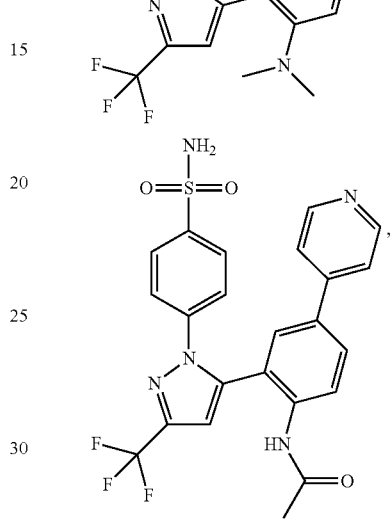
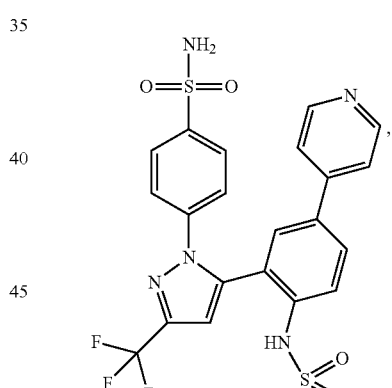
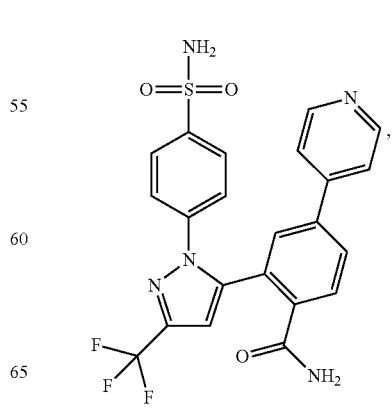

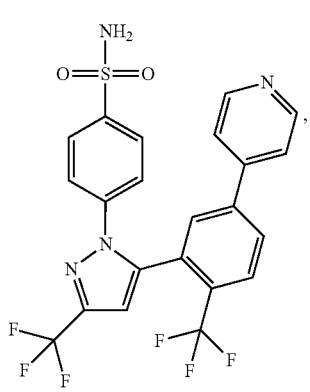
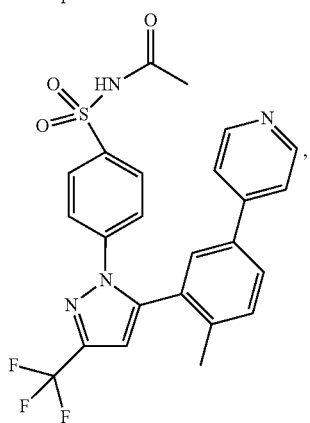
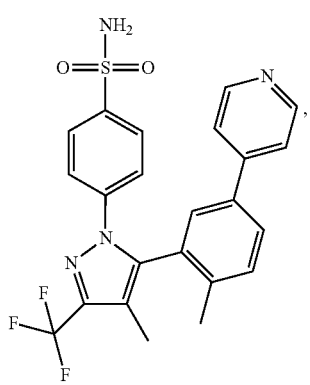
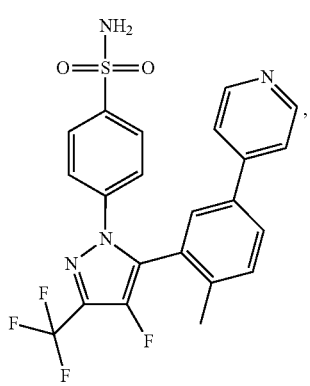
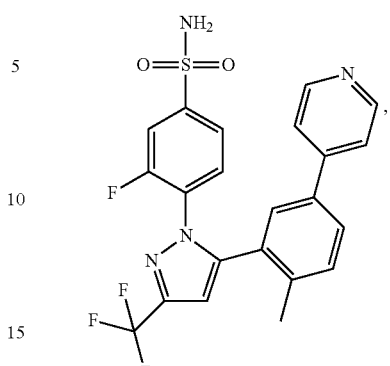
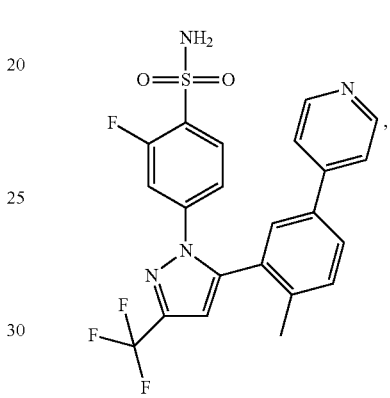
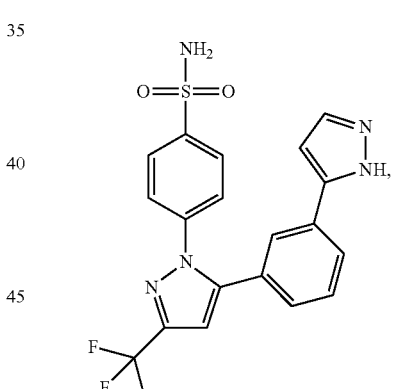
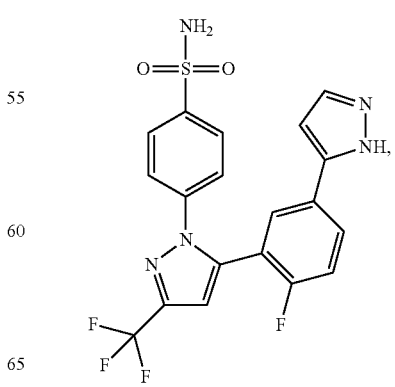

-continued
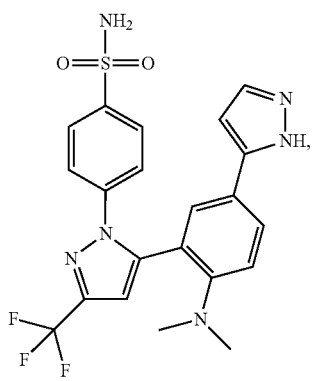
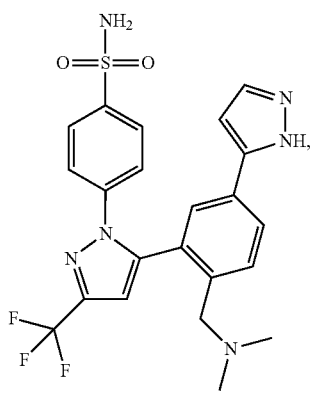
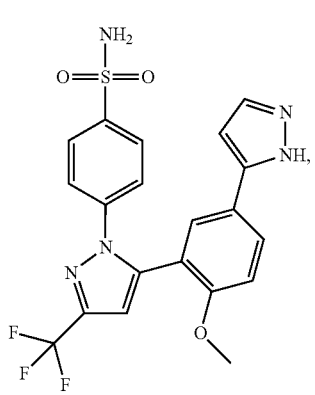
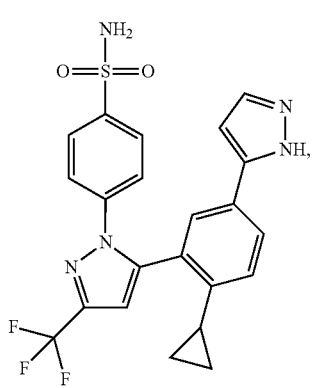
-continued
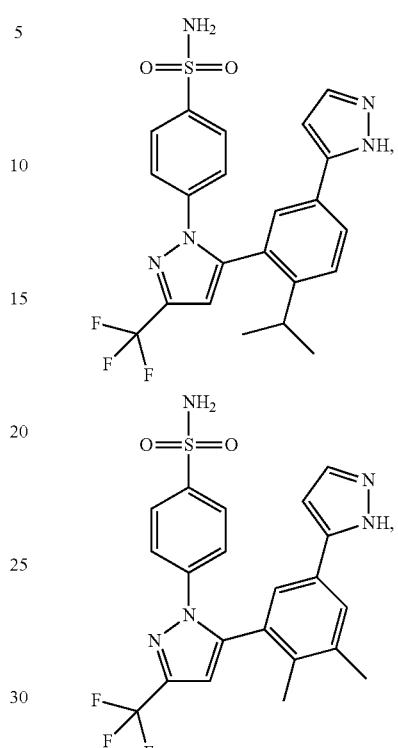
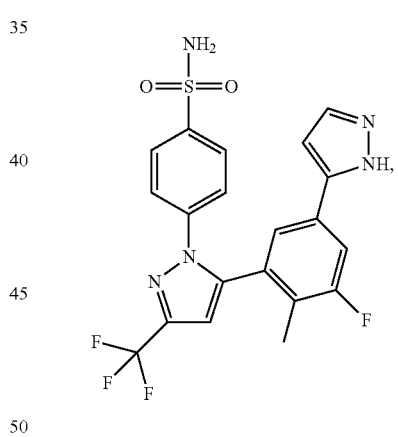
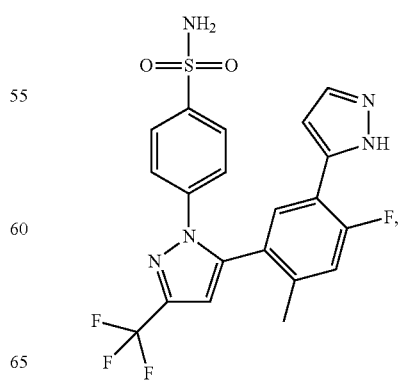

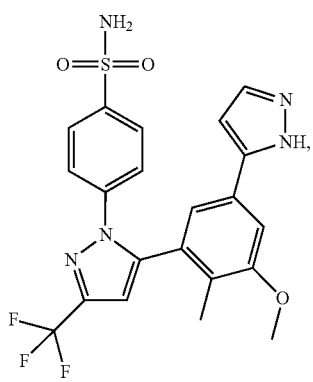
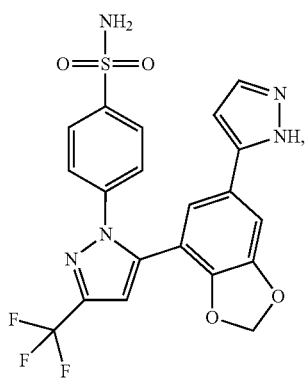
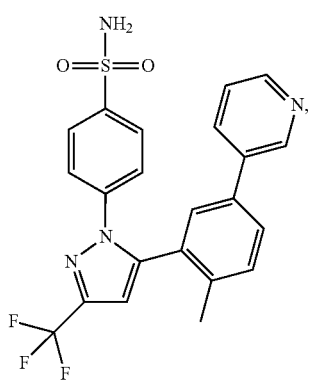
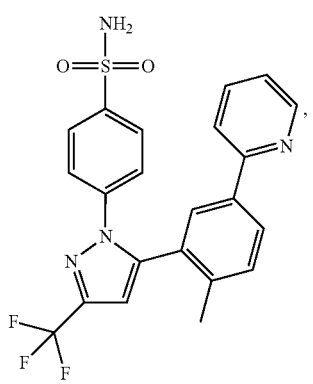
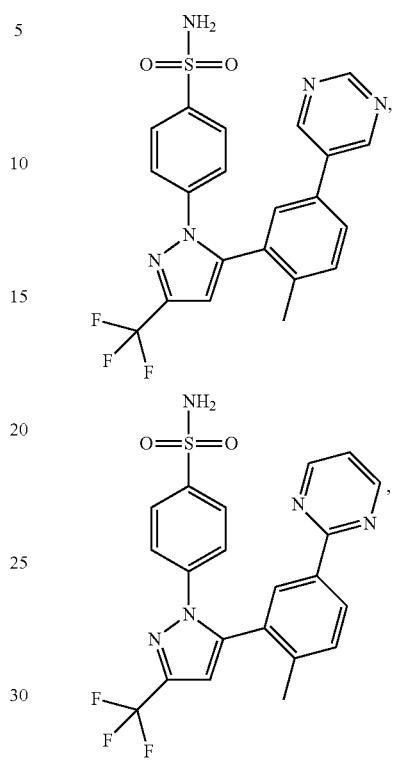
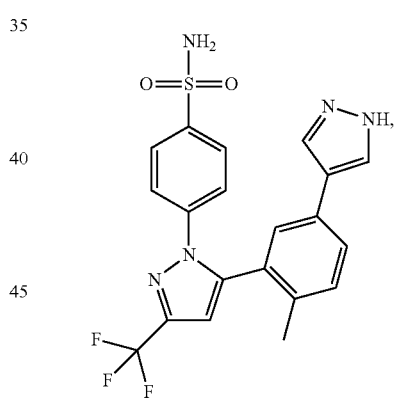
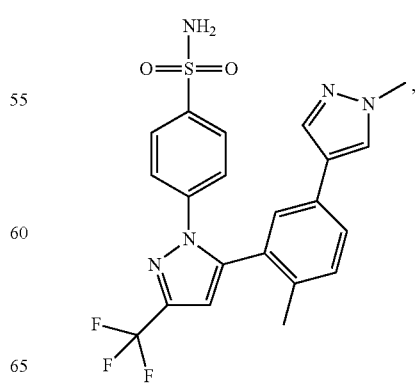

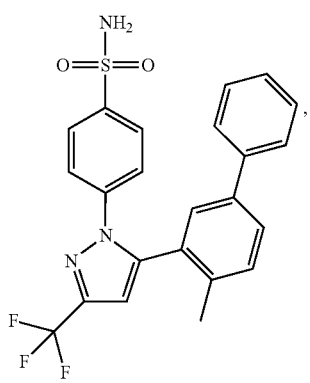
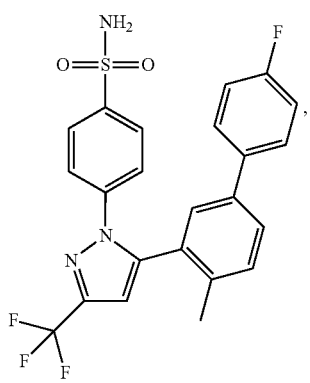
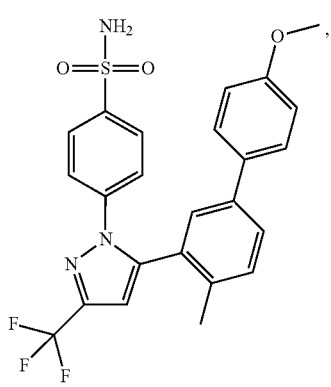
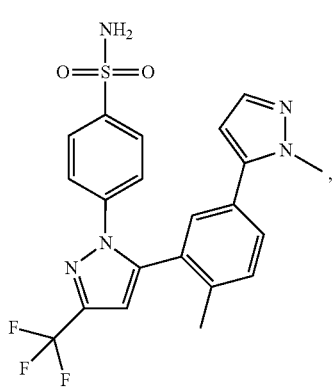
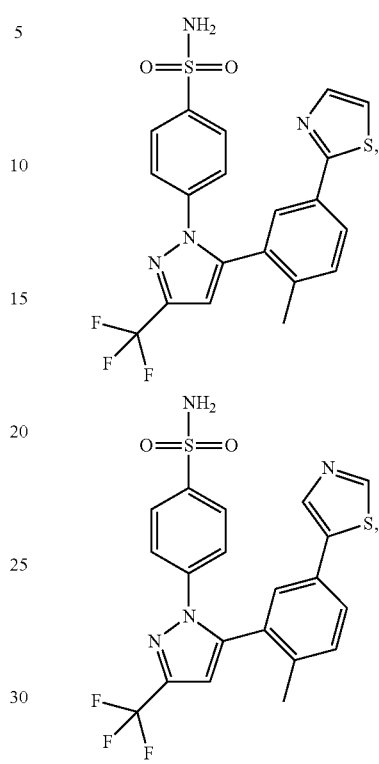
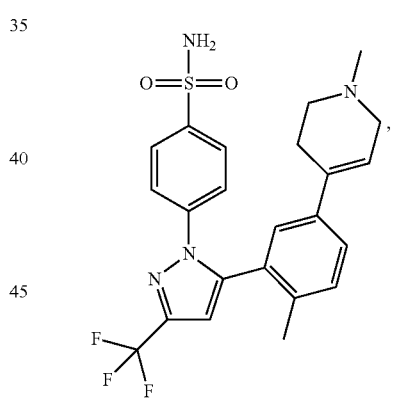
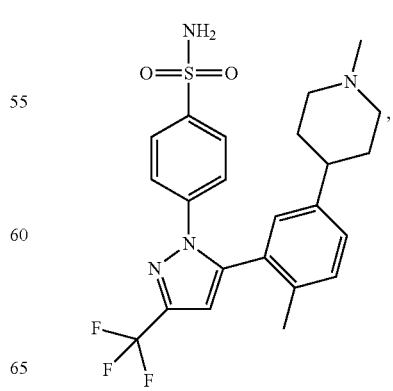

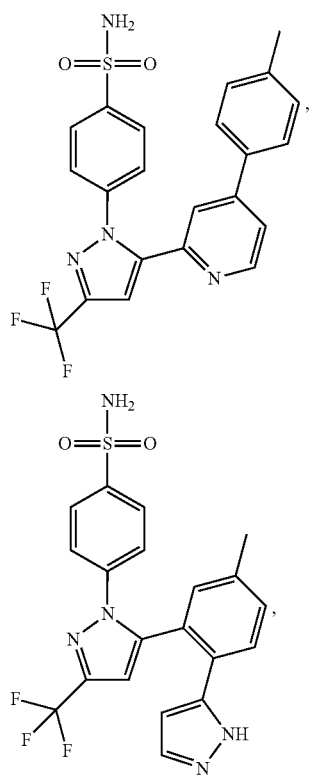
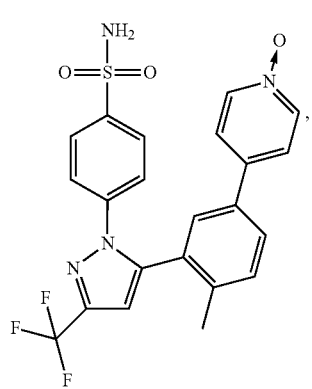
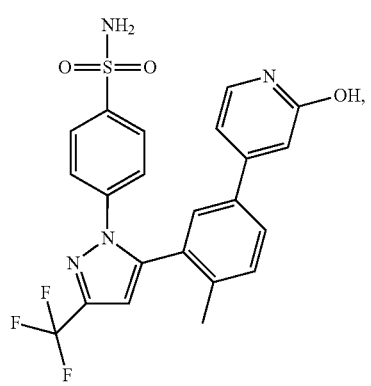
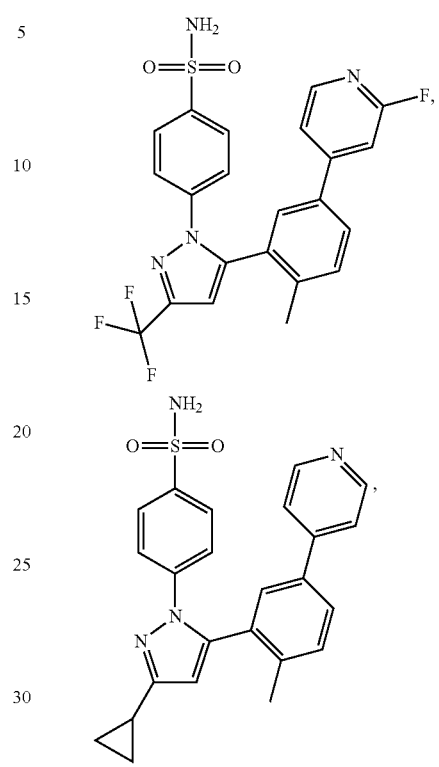
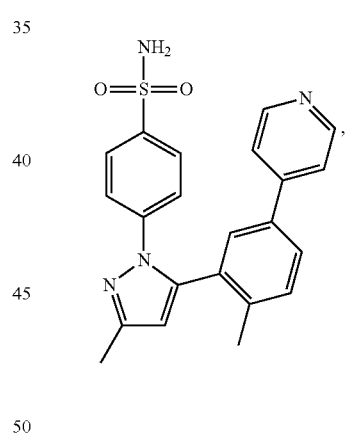
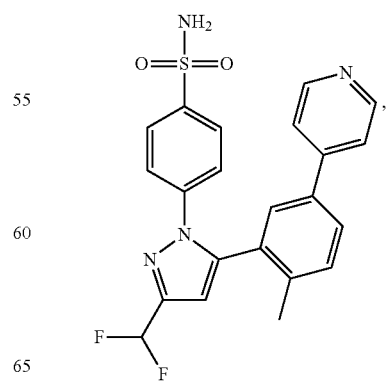

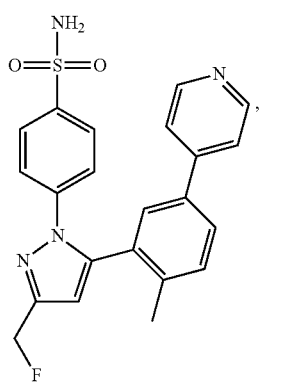
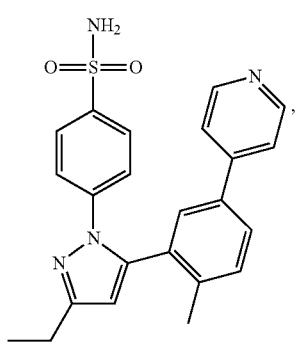
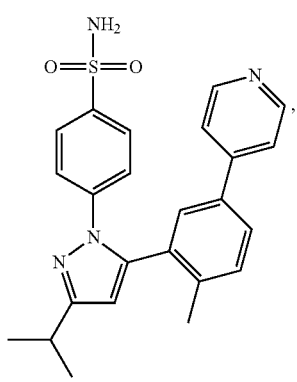
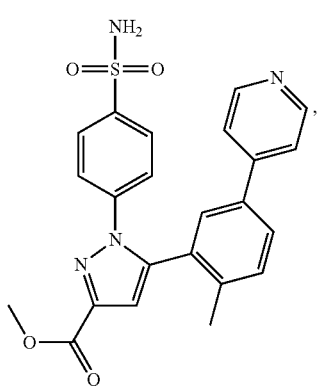
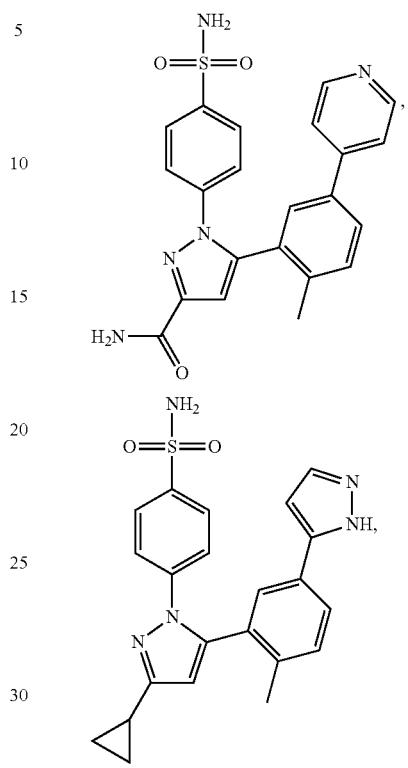
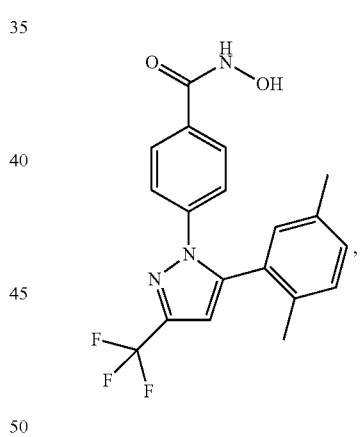
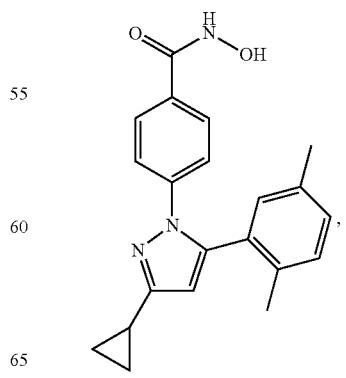

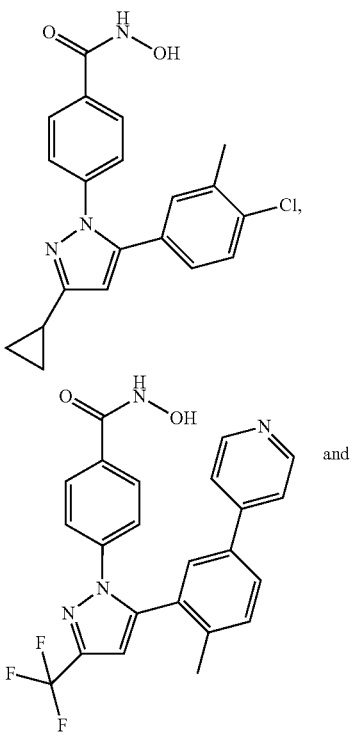

and

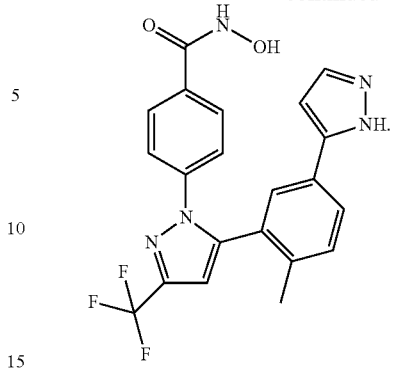

14. A method for treating a hyper-proliferative disease comprising the administration of the compound of claim 1 to a subject in need of treatment.

15. A pharmaceutical composition comprising:
   a. the compound of claim 1; and
   b. at least one pharmaceutically acceptable excipient.

16. A method for treating a hyper-proliferative disease comprising the administration of the pharmaceutical composition of claim 15 to a subject in need thereof.

17. The method of claim 14, wherein the hyper-proliferative disease comprises cancer.

18. The method of claim 16, wherein the hyper-proliferative disease comprises cancer.

* * * * *